United States Patent
Glossop et al.

(10) Patent No.: US 8,948,845 B2
(45) Date of Patent: Feb. 3, 2015

(54) SYSTEM, METHODS, AND INSTRUMENTATION FOR IMAGE GUIDED PROSTATE TREATMENT

(75) Inventors: Neil David Glossop, Toronto (CA); Bradford Johns Wood, Potomac, MD (US)

(73) Assignees: Koninklijke Philips N.V., Eindhoven (NL); The United States of America as represented by the Secretary, Dept. of Health and Human Services, Washington, DC (US)

(*) Notice: Subject to any disclaimer, the term of this patent is extended or adjusted under 35 U.S.C. 154(b) by 1595 days.

(21) Appl. No.: 11/694,280

(22) Filed: Mar. 30, 2007

(65) Prior Publication Data

US 2007/0232882 A1  Oct. 4, 2007

Related U.S. Application Data

(60) Provisional application No. 60/787,515, filed on Mar. 31, 2006.

(51) Int. Cl.
*A61B 5/05* (2006.01)
*A61B 19/00* (2006.01)
(Continued)

(52) U.S. Cl.
CPC ............ *A61B 19/5244* (2013.01); *A61B 8/0841* (2013.01); *A61B 8/4245* (2013.01); *A61B 17/3211* (2013.01); *A61B 19/52* (2013.01); *A61B 8/0833* (2013.01); *A61B 17/320092* (2013.01);
(Continued)

(58) Field of Classification Search
USPC .................. 600/407, 410, 424, 425, 437, 462; 424/9.3
See application file for complete search history.

(56) References Cited

U.S. PATENT DOCUMENTS

| 6,785,571 B2 * | 8/2004 | Glossop ...................... 600/424 |
| 2003/0040782 A1 * | 2/2003 | Walker et al. ................. 607/105 |

(Continued)

FOREIGN PATENT DOCUMENTS

WO   WO2006057786   6/2006

OTHER PUBLICATIONS

Dotan Knaan et al, "Effective intensity-Based 2D/3D Rigid Registration Between Fluoroscopic X-Ry and CT", MICCAI (1) 2003: 351-358.

(Continued)

*Primary Examiner* — Christopher Cook

(57) ABSTRACT

The invention provides systems, methods, and instrumentation for aiding the performance of an image guided procedure of the anatomy of a patient such as, for example, the prostate. The invention includes a plurality of lumens therein and a balloon portion or other fixating portion. In some embodiments, the catheter includes a lumen for introducing a contrast agent visible to an imaging modality external to the anatomy of the patient. Image space data of the catheter within the anatomy of the patient may be obtained using the imaging modality. The catheter also includes at least a lumen for inserting a registration device for obtaining patient space data regarding the anatomy of the patient. Other lumens and/or other elements visible to the imaging modality may be used. The image space data may be registered to the patient space data for use during an image guided procedure to the anatomy of the patient.

38 Claims, 18 Drawing Sheets

(51) Int. Cl.
  *A61B 8/08* (2006.01)
  *A61B 8/00* (2006.01)
  *A61B 17/3211* (2006.01)
  *A61B 17/32* (2006.01)
  *A61B 18/14* (2006.01)
  *A61B 17/28* (2006.01)

(52) U.S. Cl.
  CPC ....... *A61B 18/148* (2013.01); *A61B 2017/2808* (2013.01); *A61B 2019/5251* (2013.01); *A61B 2019/5276* (2013.01); *A61B 2019/5291* (2013.01); *A61B 2019/5483* (2013.01)
  USPC ........... 600/424; 600/410; 600/420; 600/425; 600/431; 600/435

(56) References Cited

U.S. PATENT DOCUMENTS

| | | | |
|---|---|---|---|
| 2004/0097805 A1* | 5/2004 | Verard et al. | 600/428 |
| 2004/0097965 A1* | 5/2004 | Gardeski et al. | 606/129 |
| 2004/0147914 A1* | 7/2004 | Kramer | 606/21 |
| 2004/0158143 A1* | 8/2004 | Flaherty et al. | 600/407 |
| 2004/0176757 A1* | 9/2004 | Sinelnikov et al. | 606/27 |
| 2005/0142163 A1* | 6/2005 | Hunter et al. | 424/423 |
| 2005/0182319 A1* | 8/2005 | Glossop | 600/424 |
| 2006/0147100 A1 | 7/2006 | Fitzpatrick | |
| 2006/0173269 A1 | 8/2006 | Glossop | |
| 2007/0106148 A1* | 5/2007 | Dumoulin | 600/410 |

OTHER PUBLICATIONS

A.H. Gee et al, "3D Ultrasound Probe Calibration Without a Position Sensor", CUED/FINFENG/TR 488 Sep. 2004 (Cambridge University, Department of Engineering, Trumpington Street, Cambridge CB2 1PZ, United Kingdom).

* cited by examiner

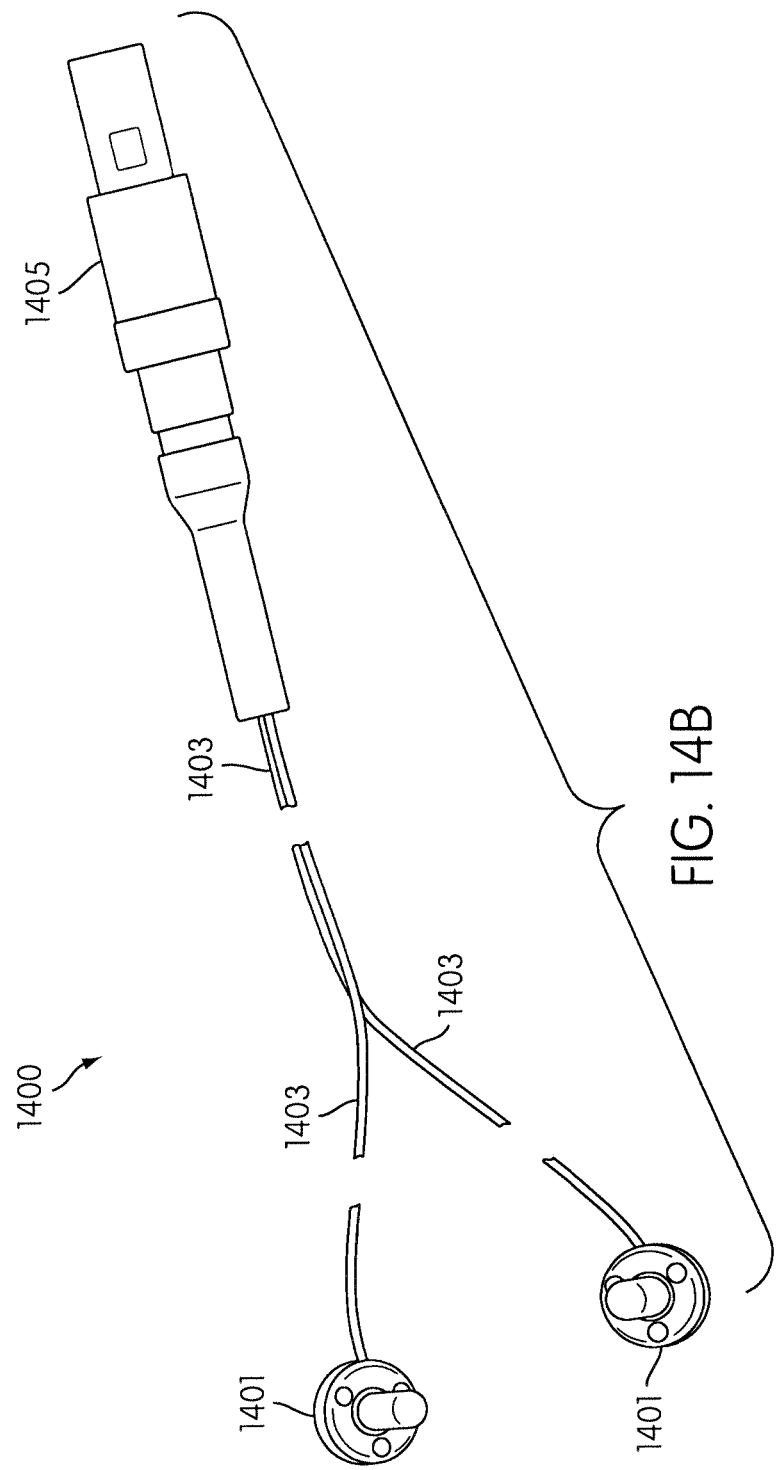

SYSTEM, METHODS, AND INSTRUMENTATION FOR IMAGE GUIDED PROSTATE TREATMENT

RELATED APPLICATIONS

This application claims priority to U.S. Provisional Patent Application Ser. No. 60/787,515, filed Mar. 31, 2006, which is hereby incorporated by reference herein in its entirety.

STATEMENT OF GOVERNMENT RIGHTS

The Government of the United States of America may have certain rights in the invention disclosed and claimed below.

FIELD OF THE INVENTION

This invention relates to a system, methods, and instrumentation for image guided prostate treatment using a modified catheter.

BACKGROUND OF THE INVENTION

Prostate cancer is the most common non-skin cancer and the second leading cause of cancer death among American men. Transrectal ultrasound guided needle biopsy is the most frequently used method for diagnosing prostate cancer due to its real-time nature, low cost, and simplicity. However, the use of ultrasound to detect prostate cancer is limited by its relatively poor image quality and low sensitivity, specifically for prostate cancers. It is difficult to use ultrasound for targeted biopsy guidance because most cancers are not visible under ultrasound. Magnetic resonance (MR) imaging is superior for visualizing the zonal anatomy of the prostate and suspicious focal lesions for prostate cancer. However, MR imaging is costly and the magnetic environment makes interventional procedures more complex, thus, making MRI imaging unsuitable for routine biopsy guidance.

Since MR and ultrasound imaging compliment each other, it is desirable when imaging the prostate to fuse preoperative MR images with real time ultrasound images and take advantage of the superior visualization of MR images in transrectal ultrasound guided biopsy. To do this, the ultrasound transducer is tracked by an exterior localizer that assigns a global coordinate system to the ultrasound images. The registration between the MRI image and the localizer may be carried out using fiducial markers either on the patient or embedded in the patient before the surgical intervention. After both MR and ultrasound are registered to the localizer, the 3D MR image can be reformatted and overlaid in the real-time 2D ultrasound image.

Performing an adequate registration can be difficult. A second problem arises if the transformation between the MR and ultrasound images is determined before the surgical intervention. The system is most accurate when the target organ is static during the procedure. Unfortunately, the prostate moves considerably during biopsy and other types of interventions. The patient often moves involuntarily due to pain or pressure related to insertion of needles or other instruments. Second, a transrectal ultrasound probe can itself cause distortion of the contour of the prostate during the procedure. Finally, respiratory motion of the patient may cause shifting of the prostate, especially when the patient is in a prone position. Since the prostate is a very small organ, the motion can easily result in a loss of accuracy in an MR/transrectal ultrasound fusion display, leading to inaccurate needle insertions when using the fused display for targeted biopsies. Sometimes, the MR and ultrasound images can be completely disconnected from each other, making the MR image useless for surgical navigation.

Accordingly, there is a need for instrumentation, systems, and method for obtaining and maintaining registration between preoperative images and intraoperative images, and determining the location of instrumentation on any of these images in patient space.

SUMMARY OF THE INVENTION

As such, the invention solves these and other problems in the art by providing improved methods and instrumentation to be used with a system for image guided surgery for performing procedures on the prostate or other areas of the anatomy of a patient.

Foley catheters are flexible (usually latex) tubes that are passed through the urethra during urinary catheterization and into the bladder to drain urine. They can be temporary or indwelling, but both function in the same manner. They are retained in the bladder by a balloon at or near the catheter tip which is inflated with sterile water. Foley catheters are used in conjunction with multiple types of procedures, including surgery. In some embodiments, the invention may utilize Foley catheters to assist in diagnostic imaging of the prostate or surrounding areas, planning treatment of the prostate or surrounding areas, and/or carrying out treatment of the prostate or surrounding areas. In some embodiments, Foley catheters or other catheters may be utilized for imaging, treatment planning, and/or treatment execution of other areas of the anatomy of a patient.

In one embodiment, the invention provides an improved Foley catheter or other catheter instrument for use in image guided procedures relating to the prostate or other areas of the anatomy of a patient. A catheter according to the invention may include a catheter tube portion, a plurality of lumens running through the catheter tube portion, a proximal end portion (that may include one or more ports for adding/removing instruments or material into/from one or more of the lumens and/or actuating one or more of the features of the catheter), a balloon or fixation portion (which may be situated at the distal end of the catheter tube portion), and/or other portions or elements.

The plurality of lumens in the catheter tube portion of the catheter may include a drainage lumen for draining urine or other fluid from a portion of the patient's anatomy, an inflation lumen for inflating the balloon or otherwise actuating the fixation portion of the catheter, a "Registration Path" lumen for insertion and use of a registration device to obtain position sensor space data, a dynamic referencing lumen to insert and/or hold a referencing device within the catheter for the purposes of dynamic referencing of the portion of the anatomy of the patient, an image coil lumen for inserting a micro imaging coil (e.g., an MR coil) into the anatomy of a patient, an instrument lumen for introducing a diagnostic or therapeutic instrument (e.g., a biopsy probe, an optical coherence tomography (OCT) probe, an injection needle, or other instrument), and/or other lumens. In some embodiments, one or more the lumens of the catheter may be multipurpose and may perform several functions.

In some embodiments, the catheter may include additional features such as, for example, the balloon portion or other portion of the catheter may include markings or other fiducial elements which may be visible to an imaging modality, one or more of the lumens described may themselves include a plurality of lumens therein, one or more position indicating elements may be incorporated into the catheter so that the catheter itself or parts thereof may serve as a registration or dynamic referencing device.

The invention also provides a process for using an enhanced catheter to obtain image and/or patient space data necessary for an image guided procedure on the prostate or other anatomy of a patient, for performing a registration of preoperative image space, live image space data, and intraoperative patient space data of the prostate or other anatomy of the patient, and/or for guiding tracked instruments to the prostate or anatomy of the patient. The invention also provides a system and methods for tracking the location of the prostate during an intervention or other study that assists in accounting for the motion of the prostate due to physician induced motion, normal physiologic patient motion, or other motion. In some embodiments, the invention provides a system and methods for integration of live imaging modalities with preoperative images (e.g., ultrasound with MR).

In some embodiments, the catheter is inserted into the anatomy of the patient proximate to the prostate or other point of interest in the anatomy of the patient. The balloon portion of the catheter is then inflated, lodging the catheter portion into the anatomy of the patient (e.g., in the opening of the bladder during prostate surgery). This fixes the location of the catheter so that it is relatively immobile near the fixation point (typically the sphincter in prostate surgery) relative to the associated anatomy.

In some embodiments, a preoperative scan may be performed that may utilize a micro magnetic resonance (MR) imaging coil placed within an image coil lumen or other lumen of the catheter. This enables MR imaging of the surrounding tissue. In some embodiments, image data may be obtained using an ultrasound transducer internal to the catheter or placed in an adjacent orifice such as, for example, the rectum. In some embodiments, additional images may be obtained using an imaging device that illustrate the position of the inserted catheter relative to the prostate (or other point of interest). In some embodiments, this image data may be obtained using an external imaging modality such as, for example, MR or other imaging modality. In some embodiments, the image data from the imaging coil internal to the catheter may be reconciled or otherwise merged (e.g., co-registered) with the image data regarding the catheter relative to the point of interest of the anatomy. The merged image data and/or the image data regarding the catheter's position in the anatomy relative to the prostate or other point of interest may be used to obtain "image space data" regarding the position of at least a portion of the catheter to the prostate or other point of interest in image space.

In some embodiments, obtaining the image data of the catheter relative to the prostate or other point of interest, may involve making at least part of the catheter visible to an imaging modality. In some embodiments, a path of the catheter may be made visible to the imaging modality through introduction of appropriately visible materials such as, for example, gadolinium ("Gd"). In some embodiment, the gadolinium or other visible material may be placed into a "Registration Path" lumen of the catheter. This visible material may be introduced after an initial diagnostic scan (e.g., during a scan using the imaging coil within the catheter) so to not obscure images of the prostate or other area of interest. Otherwise the visible material may be introduced during the diagnostic scan, during a second diagnostic scan, or intraoperatively. In some embodiment, material visible to the imaging modality need not be introduced into the catheter, if for example, the catheter includes a lumen in which Gd or other visible material or feature is already present or the catheter material itself is visible under the modality.

In some embodiments, elements such as fiducials visible to one or more of the imaging modalities used with the invention may be placed in or on the balloon portion, which would make at least part of the fixed distal portion of the catheter visible under the imaging modality. In some embodiments, these fiducials or other elements could be made to form a pattern in part of the balloon. In some embodiments, these fiducials or other elements may include, at least in part, sub-balloons inflated inside the main balloon but containing a fluid that is visible under the imaging modality. In some embodiments, the fiducials or other elements may comprise a special path/lumen (e.g., may be part of the "Registration Path" lumen that may be housed within the balloon or interior of the catheter) such as a spiral or other tortuous pattern that is made visible through injection of a contrast agent. Other things can be done to the balloon or the catheter or part thereof to render it visible to the imaging modality.

Once the positions of the imageable portions of the catheter are obtained in image space, their spatial position and/or orientation in patient space (i.e. position sensor space) may be obtained. In some embodiments, the position sensor space information may be done by using a drag-back method as described in U.S. Patent Publication No. 20050182319, entitled "Method and Apparatus for Registration, Verification, and Referencing of Internal Organs (U.S. patent application Ser. No. 11/059,336), which is hereby incorporated by reference herein in its entirety, by placing a tracked guidewire or similar device into the catheter (e.g., into the "Registration Path" lumen) and sliding it over the zone wherein the catheter is imageable while sampling patient space coordinates of the guidewire. Other techniques may be used to obtain position sensor space information. In some embodiments, a "measurement catheter" in which multiple sensors that are located at locations that are known in relation to imageable portions of the catheter may be inserted into one of the catheter lumens to effect registration.

The image space information and the patient space information (position sensor space information) may be registered to one another to obtain a transformation matrix that may be used to guide tracked instruments for image guided procedures.

In some embodiments, dynamic referencing may be performed by parking (i.e., "fixing") position sensing elements in the balloon portion or a dynamic referencing lumen of the catheter. Dynamic referencing tracks the motion of the organ or other anatomy of the patient during a treatment. In some embodiment, the position sensing elements used for registration may be used for dynamic referencing. In some embodiments, a measurement catheter used in registration may be left in the catheter to assist in compensating or measuring motion of the prostate.

As mentioned above, a therapeutic instrument or other tracked tool may be inserted into the anatomy of the patient and navigated to the prostate or other point of interest using a graphical overlay of the tracked portion of the instrument superimposed on images of the anatomy of the patient (e.g., the images obtained using the micro image coil and/or the images used to determine the position of the imageable elements of the catheter relative to the prostate). Tracked therapeutic instruments may include, for example, one or more of a tracked radiofrequency ablation devices, a tracked cryo-ablation probe, a tracked microwave ablation device, a tracked high definition radiation therapy (HDRT) device, a tracked high intensity focused ultrasound (HIFU), a tracked needle for insertion of brachytherapy seeds, a tracked needle for other therapeutic purposes, a tracked scalpel, a tracked harmonic scalpel, a tracked clamp, a tracked Bovey device or other electrocautery device, a tracked endorectal needle guide, and/or other tracked instrument.

In some embodiments, the invention may include an integrated image guided surgery system that enables image guided therapy or procedures using the instrumentation discussed herein. In some embodiments, the integrated system may include a computer element which may comprise one or more of a processor, a memory device, a power source, a control application, one or more software modules, one or more inputs/outputs, a display device, a user input device, and/or other elements. In some embodiments, the integrated system may also include a registration device, a referencing device, a tracking device, an imaging device, one or more tracked therapeutic instruments, and/or other elements.

The various objects, features, and advantages of the invention will be apparent through the detailed description and the drawings attached hereto. It is also to be understood that the following detailed description is exemplary and not restrictive of the scope of the invention.

BRIEF DESCRIPTION OF THE DRAWINGS

FIG. 14B illustrates an example of a skin patch device according to various embodiments of the invention.

DETAILED DESCRIPTION OF PREFERRED EMBODIMENTS

The invention provides a system, methods, and instrumentation for using an enhanced catheter to obtain image and/or patient space data necessary for an image guided procedure on the prostate or other anatomy of a patient, for performing a registration of image space and patient space data of the prostate or other anatomy of the patient, and/or for guiding tracked instruments to the prostate or anatomy of the patient.

Figure 1:
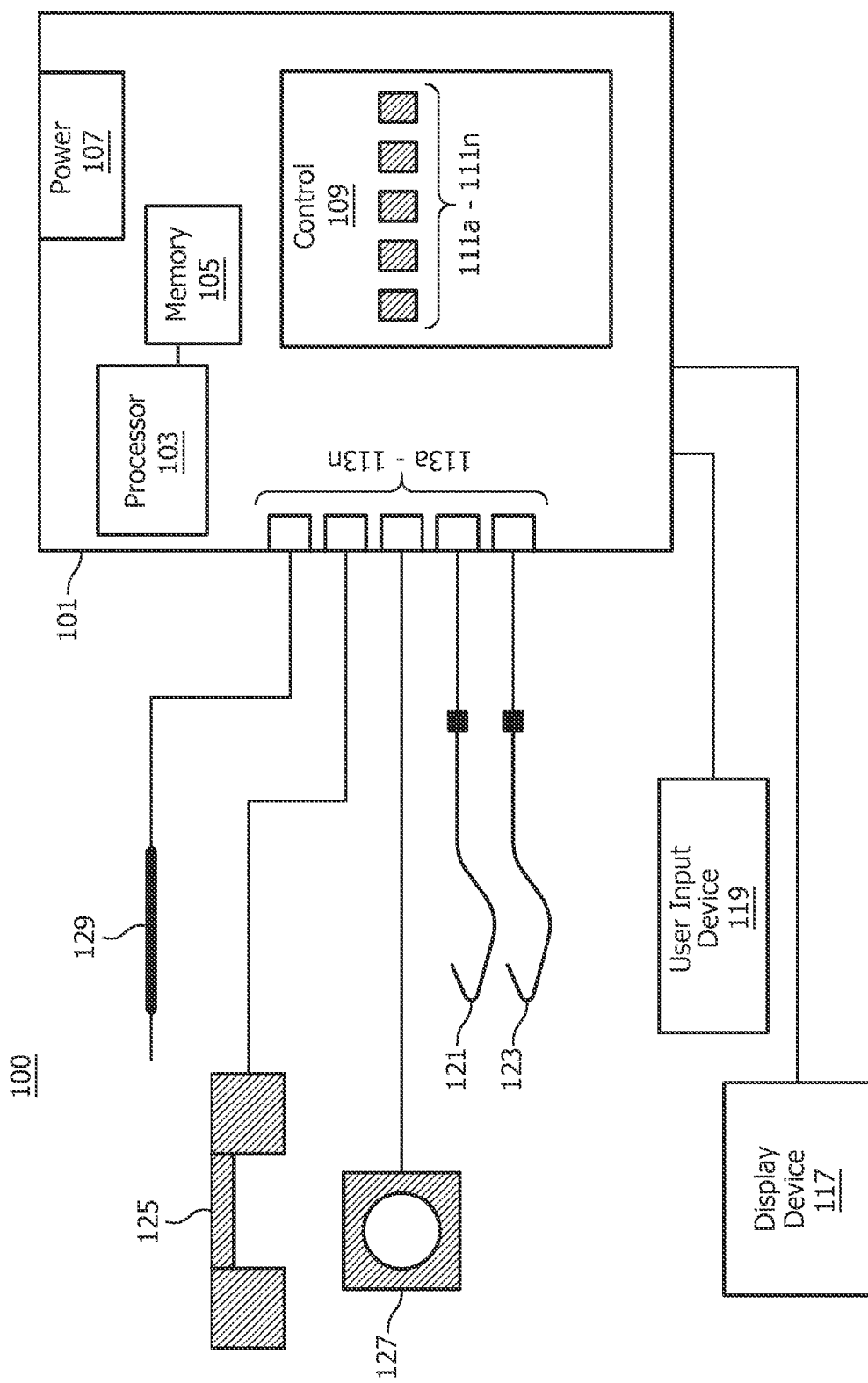
FIG. 1 illustrates an example of an integrated system for image guided procedures according to various embodiments of the invention.

FIG. 1 illustrates a system 100, which is an example of an integrated system for image guided surgery according to an embodiment of the invention. System 100 includes a computer element 101, a registration device 121, a referencing device 123, a tracking device 125, an imaging device 127, a tracked instrument 129, and/or other elements.

Computer element 101 may include a processor 103, a memory device 105, a power source 107, a control application 109, one or more software modules 111a-111n, one or more inputs/outputs 113a-113n, a display device 117, a user input device 119, and/or other elements.

Computer element 101 may include one or more servers, personal computers, laptop computers, or other computer devices. Computer element 101 may receive, send, store, and/or manipulate any data necessary to perform any of the processes, calculations, or operations described herein. Computer element 101 may also perform any processes, calculations, or operations necessary for the function of the devices, elements, instruments, or apparatus described herein.

In some embodiments, computer element 101 may host a control application 109. Control application 109 may comprise a computer application which may enable one or more software modules 111a-111n. One or more software modules 111a-111n enable processor 103 to receive, send, and/or manipulate imaging data regarding the location, position, and/or coordinates of one or more instruments, devices, detectable elements, position indicating elements, or other elements of the invention inside an anatomical region of a patient. This imaging data may be stored in memory device 105 or other data storage location.

In some embodiments, one or more software modules 111a-111n may also enable processor 103 to receive, send, and/or manipulate data regarding the location, position, orientation, and/or coordinates of one or more position indicating elements or other elements of the invention inside the anatomical region of the patient. This data may be stored in memory device 105 or other data storage location.

In some embodiments, one or more software modules 111a-111n may also enable processor 103 to calculate one or more registration transformations, perform registration (or mapping) of coordinates from two or more coordinate systems according to the one or more transformation calculations, and produce one or more images from registered data. In some embodiments, images produced from image data, position data, registration data, other data, or any combination thereof may be displayed on display device 117.

In some embodiments, one or more software modules 111a-111n may also enable processor 103 to receive, send, and/or manipulate data regarding the location, orientation, position, and/or coordinates of one or more position indicating elements for use in constructing a rigid-body description of an anatomical region of a patient. In some embodiments, one or more software modules 111a-111n may enable processor 103 to create dynamic, deformable, and/or other models of an anatomical region of the patient, and may enable the display of real time images regarding the anatomical region. In some embodiments, one or more software modules 111a-111n may enable processor 103 to create and display merged preoperative and intraoperative images. In some embodiments, these images may be displayed on display device 117. In some embodiments, one or more software modules 111a-111n may enable the generation and display of images of the anatomy of the patient with the position and/or orientation of a tracked instrument superimposed thereon in real time (such that motion of the tracked instrument within the anatomy of the patient is indicated on the superimposed images) for use in an image guided procedure. In some embodiments, one or more software modules 111a-111n may enable reformatting of magnetic resonance images and dynamic graphic overlay of reformatted magnetic resonance images on ultrasound images.

In some embodiments, integrated system 100 may include a registration device 121. In some embodiments, registration device 121 may be operatively connected to computer element 101 via an input/output 113. In some embodiments, registration device 121 need not be operatively connected to computer element 101, but data may be sent and received between registration device 121 and computer element 113. Registration device 121 may, inter alia, aid in providing, image data, location data, position data, and/or coordinate data regarding an anatomical region of the patient or one or more elements of the invention within the anatomical region of the patient. The registration device may otherwise enable registration of the anatomical region the patient, (including soft tissues and/or deformable bodies) and may include one or more position indicating elements (e.g., sensor coils) whose position and/or orientation are trackable by tracking device 125 in the coordinate system of tracking device 125.

In some embodiments, integrated system 100 may include a referencing device 123. In some embodiments, referencing device 123 may be operatively connected to computer element 101 via an input/output 113. In some embodiments, referencing device 123 need not be connected to computer element 101, but data may be sent and received between referencing device 123 and computer element 113. Referencing device 123 may, inter alia, aid in providing image data, location data, position data, coordinate data, and/or motion data regarding an anatomical region of the patient or one or more elements of the invention within the anatomical region of the patient. Referencing device 123 may otherwise enable dynamic referencing of an anatomical region of a patient, (including soft tissues and/or deformable bodies) and may include one or more position indicating elements (e.g., sensor coils) whose position and/or orientation are trackable by tracking device 125 in the coordinate system of tracking device 125. In some embodiments, registration device 121 and referencing device 123 may be combined into a single device.

In one embodiment, integrated system 100 may include a tracking device 125. In one embodiment, tracking device 125 may be operatively connected to computer element 125 via an input/output 113. In some embodiments, tracking device 125 need not be operatively connected to computer element 125, but data may be sent and received between tracking device 125 and computer element 113. Tracking device 125 may include an electromagnetic tracking device, global positioning system (GPS) enabled tracking device, an ultrasonic tracking device, a fiber-optic tracking device, an optical tracking device, radar tracking device, or other type of tracking device. Tracking device 125 may be used to obtain data regarding the three-dimensional location, position, coordinates, and/or other information regarding one or more position indicating elements within an anatomical region of the patient. Tracking device 125 may provide this data/information to computer element 801. In some embodiments, the position indicating elements tracked by tracking device 125, may be placed on or integrated in registration device 121, referencing device 123, tracked instrument 129, and/or other elements. In some embodiments, tracking device 125 may be able to track the position and/or orientation of a micro-imaging coil (e.g., an MR coil) within the anatomy of the patient in the coordinate system of the tracking device.

In some embodiments, integrated system 100 may include an imaging device 127. In one embodiment, data may be sent and received between imaging device 127 and computer element 113. This data may be sent and received via an operative connection, a network connection, a wireless connection, through one or more floppy discs, or through other data transfer methods. Imaging device 127 may be used to obtain image data, position data, or other data necessary for enabling the apparatus and processes described herein. Imaging device 127 may provide this data to computer element 101. Imaging device 127 may include x-ray equipment, computerized tomography (CT) equipment, positron emission tomography (PET) equipment, magnetic resonance imaging (MRI) equipment, fluoroscopy equipment, ultrasound equipment, an isocentric fluoroscopic device, a rotational fluoroscopic reconstruction system, a multislice computerized tomography device, an intravascular ultrasound imager, an optical coherence tomography (OCT) device, a single photon emission computed tomography device, a magnetic resonance imaging device, or other imaging/scanning equipment.

Integrated system 100 may also include one or more tracked instruments 129. A tracked instrument 129 may include an instrument for providing a therapy, sampling or otherwise removing or ablating tissue, or otherwise investigating or providing therapy to a portion of the anatomy of a patient. For example, tracked instrument 129 may be or include a tracked probe, a tracked radiofrequency ablation probe, a tracked cryo-ablation probe, a tracked microwave device, a tracked high definition radiation therapy (HDRT) needle, a tracked needle for insertion of brachytherapy seeds (or other therapy device or substance), a tracked scalpel, a tracked harmonic scalpel, a tracked clamp, a tracked linear accelerator, a tracked radiation therapy treatment couch, a tracked high frequency focused ultrasound (HIFU), a tracked Bovey device or other electrocautery device, a tracked endorectal needle guide, a tracked Foley catheter or other tracked catheter, a tracked guidewire, and/or other tracked device. In some embodiments, tracked instrument 129 may include one or more position indicating elements on or integrated therein. The position, location and/or orientation of the position indicating elements may be determined or tracked by tacking device 125.

In some embodiments, integrated system 100 may include, interface with and/or otherwise communicate with one or more additional devices and/or elements such as, for example, temperature sensors, pressure sensors, motion sensors, electrical sensors, EMG equipment, ECG equipment, or other equipment or sensors.

In some embodiments, one or more tracked instruments 129, registration devices 121, referencing devices 123, and/or other elements or devices described herein may be coupled to an imaging device or component thereof such as, for example, an ultrasound transducer handle or CT gantry or couch.

In some embodiments, one or more tracked instruments 129, registration devices, referencing devices, and/or other elements or devices described herein may be interchangeably "plugged into" one or more inputs/outputs 113a-113n. In some embodiments, various software, hardware, and/or firmware may be included in integrated system 100, which may enable various imaging, referencing, registration, navigation, diagnostic, therapeutic, or other instruments to be used interchangeably with integrated system 100. In some embodiments, the software, firmware, and/or other computer code necessary to utilize various elements described herein such as, for example, display device 117, user input 119, registration device 121, referencing device 123, tracking device 125, imaging device 127, tracked instrument 129 and/or other device or element, may be provided by one or more of modules 111a-111n.

Examples of instruments that may be used with integrated system 100 as tracked instruments 129 are illustrated in FIGS. 2 through 18. Tracked instruments 129 such as these and others may include or may be outfitted with one or more position indicating elements whose position and/or orientation can be tracked by tracking device 125. Instruments that include or are outfitted with position indicating elements may be considered "tracked instruments." In some embodiments, the position indicating elements of tracked instruments 129 may be or include electromagnetic sensor coils that are trackable by tracking device 125.

In some embodiments, a tracked instrument 129 may include a single position indicating element. In some embodiments, a tracked instrument 129 may include multiple position indicating elements. For example, if two or more 5-degree-of-freedom position indicating elements are used, the position indicating elements may be oriented with respect to one another on the instrument such that the relative positions of the position indicating elements may be determined to create an instrument capable of being tracked in all 6-degrees-of-freedom (i.e., (X, Y, Z) location (also referred to herein as "position"), as well as roll, pitch, and yaw orientation). For example, when multiple 5-degree-of-freedom position indicating elements are used, they may in some embodiments be placed perpendicular to one another. Tracked instrument 129 may then be calibrated to tracking device 125 by determining the location of the instrument tip relative to the position indicating elements, and in some embodiments, a plane and coordinate system associated with tracked instrument 129.

Figure 2:
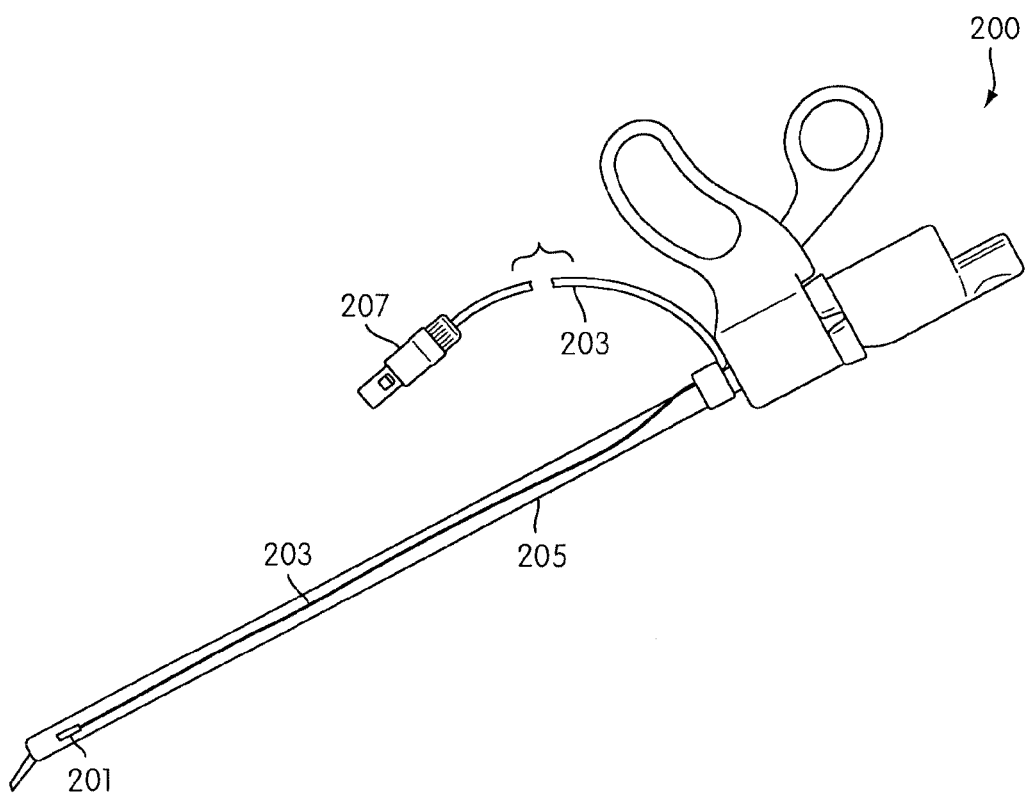
FIG. 2 illustrates an example of a tracked instrument according to various embodiments of the invention.
Figure 3:
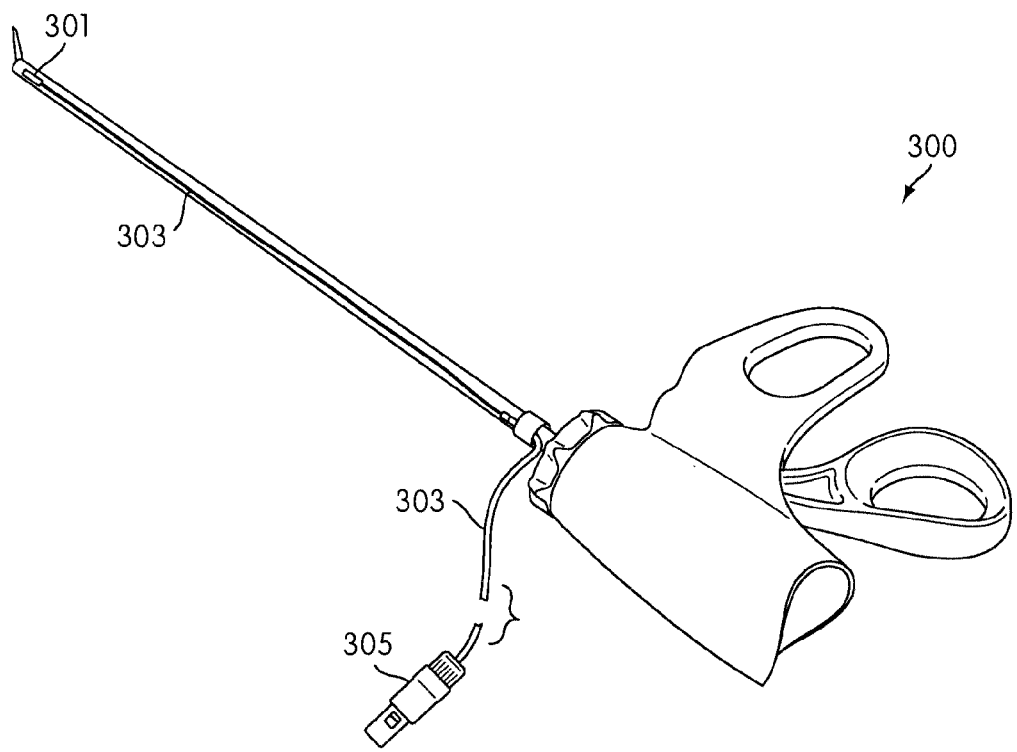
FIG. 3 illustrates an example of a tracked instrument according to various embodiments of the invention.

Examples of tracked instruments 129 may include harmonic scalpels that include one or more position indicating elements or harmonic scalpels onto which one or more position indicating elements have been fixed. FIG. 2 illustrates an harmonic scalpel 200, which is an example of a tracked instrument 129 according to various embodiments of the invention. Harmonic scalpel 200 includes a position indicating element 201, which renders harmonic scalpel 200 a tackable instrument that is trackable by tracking system 125. Harmonic scalpel 200 also includes one more leadwires 203 that are secured to shaft 205 of harmonic scalpel and ultimately extend off of the body of harmonic scalpel 200 and terminate in an interface 207 (e.g., a plug that may be connected to an input 113 of integrated system 100). Leadwires 203 serve to provide an operative connection from position indicating element 201 to integrated system 100 via interface 207 and an input 113. FIG. 3 illustrates a harmonic scalpel 300, which is another example of a tracked instrument 129, according to various embodiments of the invention. Harmonic scalpel 300 may include a position indicating element 301, leadwires 301, and an interface 305.

Figure 4A:
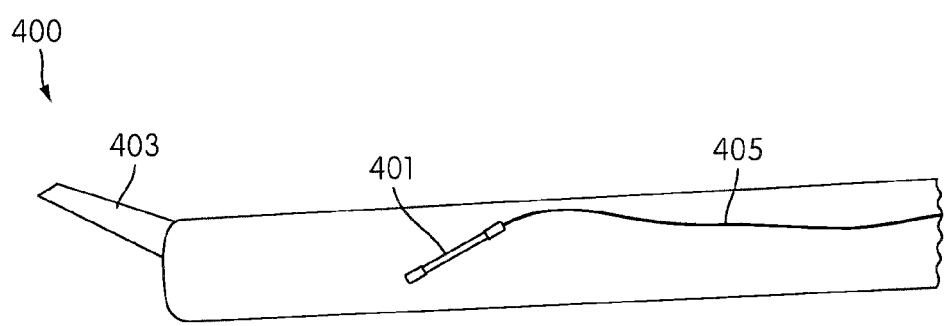
FIG. 4A illustrates an example of a tracked instrument according to various embodiments of the invention.
Figure 4B:
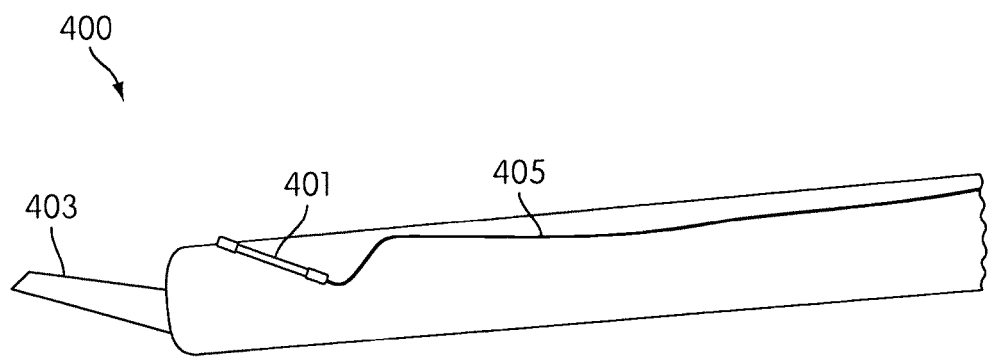
FIG. 4B illustrates an example of a tracked instrument according to various embodiments of the invention.

In some embodiments, one or more of the one or more position indicating elements are placed near the tip of tracked instrument 129. Whereas its therapeutic or sampling element may be located at the tip and it may desirable to tack the therapeutic or sampling element. For example, FIG. 4A illustrates an example of the tip portion 400 of an harmonic scalpel outfitted with a position indicating element 401 near the end of tip portion 400 and near to scalpel portion 403 of the instrument. Additional position indicating elements may also be placed near the tip or along the shaft. FIG. 4A also illustrates leadwires 405 leading from position indicating element 401 along the shaft of the instrument. FIG. 4B illustrates tip portion 400 of the harmonic scalpel that is outfitted with a position indicating element 401 situated closer to the end of tip portion 400 and scalpel portion 403 of the instrument. In some embodiments, more than one position indicating element of a tracked instrument are placed near the therapeutic or sampling element of an instrument. This may enable the device to be tracked more accurately or with more degrees of freedom than possible using a single sensor element. Additionally, the closer to the therapeutic end of the instrument a position indicating element is located, the more accurately a user can use integrated system 100 to guide the therapeutic or sampling element to the desired point in a patient's anatomy.

Figure 4C:
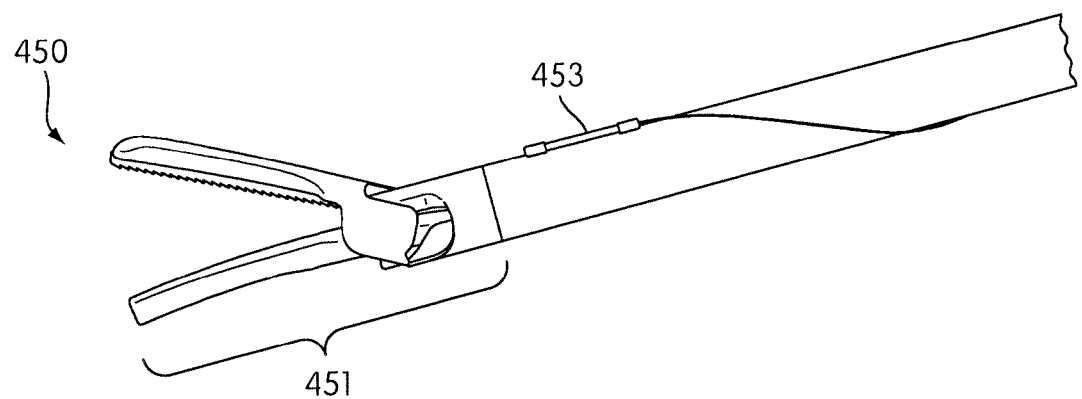
FIG. 4C illustrates an example of a tracked instrument according to various embodiments of the invention.

In some embodiments, the therapeutic or sampling element of a tracked instrument may necessitate that a position indicating element or elements located at the tip of the instrument be moved further or closer away from the actual end of the instrument. For example, FIG. 4C illustrates a tip portion 450 of a harmonic scalpel that includes a scalpel portion 451 that takes up more room at the end of the tip portion 450. As such, position indicating element 453 is located slightly farther back from the end of tip portion 450.

Figure 5:
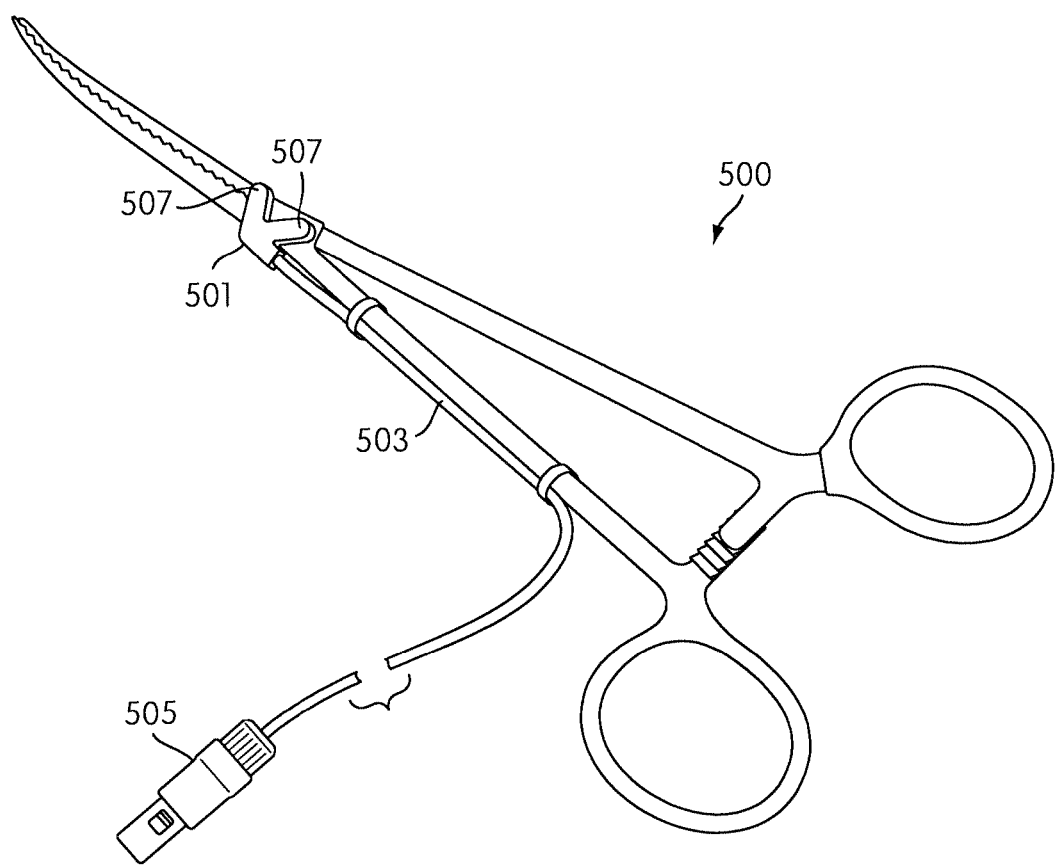
FIG. 5 illustrates an example of a tracked instrument according to various embodiments of the invention.

Another example of a tracked instrument 129 that may be used with integrated system 100 is a Kelley clamp onto which one or more position indicating elements have been attached. FIG. 5 illustrates a Kelly clamp 500 with two position indicating elements attached thereto. The two position indicating elements may be housed in an element 501. Additionally, leadwires 503 may lead from element 501 along Kelly clamp 500 and ultimately extend off of the body of Kelly clamp 500 and terminate in an interface 505 (e.g., a plug that may be connected to an input 113 of integrated system 100). In some embodiments, the position indicating elements of Kelly clamp 500 may be positioned perpendicular from one another within one of two arms 507 of element 501. As such, two 5-degree-of-freedom position indicating elements may be used to provide a tracked instrument that enables determination of 6 degrees of freedom. Furthermore, position indicating elements of Kelly clamp 500 enable the tip, the clamping region, and the clamping plane of the clamp to be determined/tracked or may enable determination of the plane that the clamping action of the clamp will effect.

Figure 6:
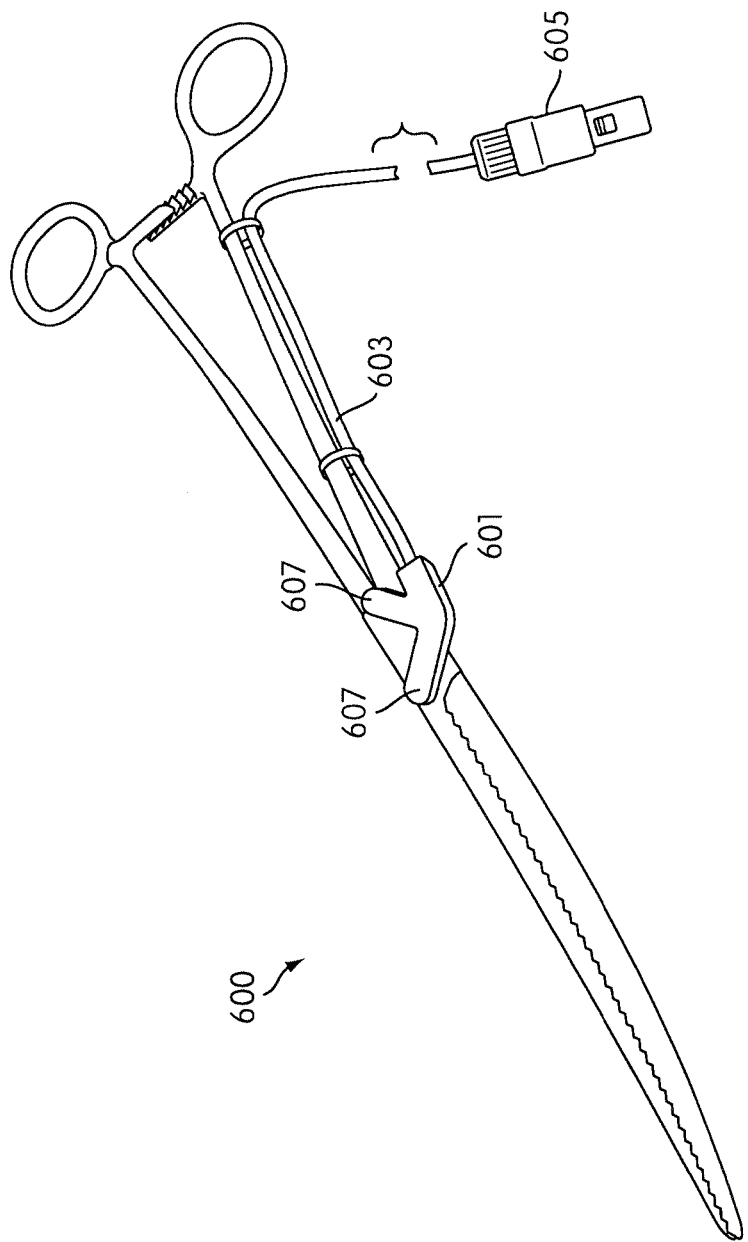
FIG. 6 illustrates an example of a tracked instrument according to various embodiments of the invention.

FIG. 6 illustrates a Kelly clamp 600, which is another example of a tracked instrument 129 for use with integrated system 100. Kelly clamp 600 includes a tracking element 601 with two arms 607, each of which includes a position indicating element, wherein the position indicating elements are oriented perpendicular to one another. Kelly clamp 600 also includes leadwires 603 that terminate in an interface 605.

Figure 7:
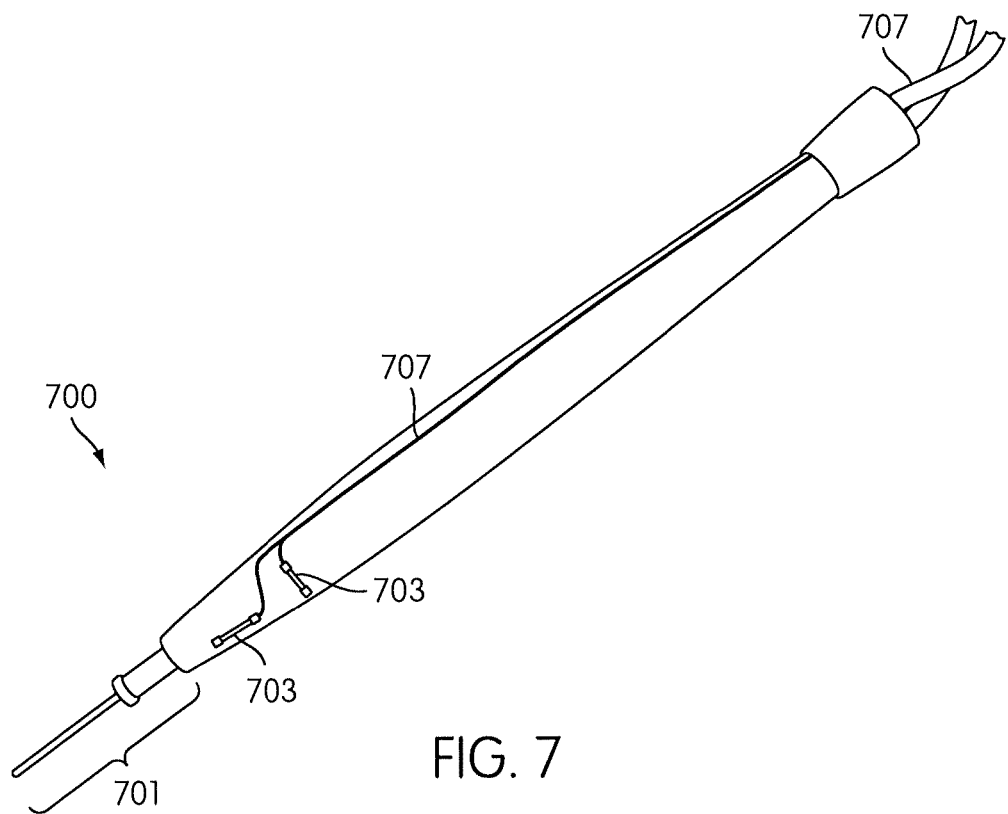
FIG. 7 illustrates an example of a tracked instrument according to various embodiments of the invention.
Figure 8:
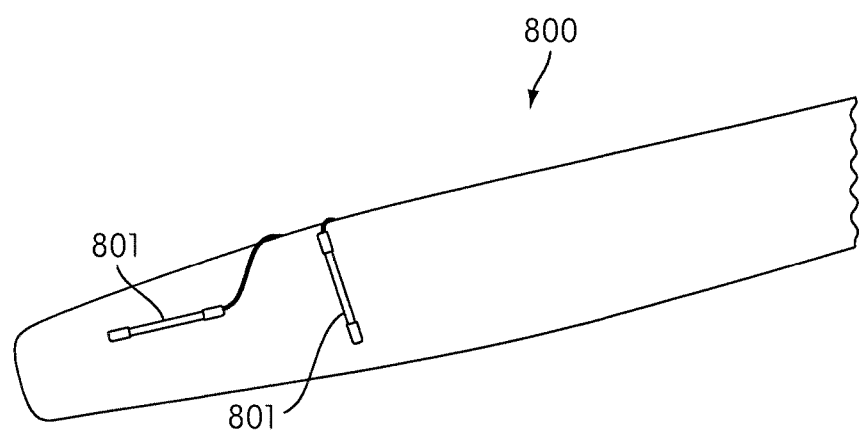
FIG. 8 illustrates an example of a tracked instrument according to various embodiments of the invention.
Figure 9:
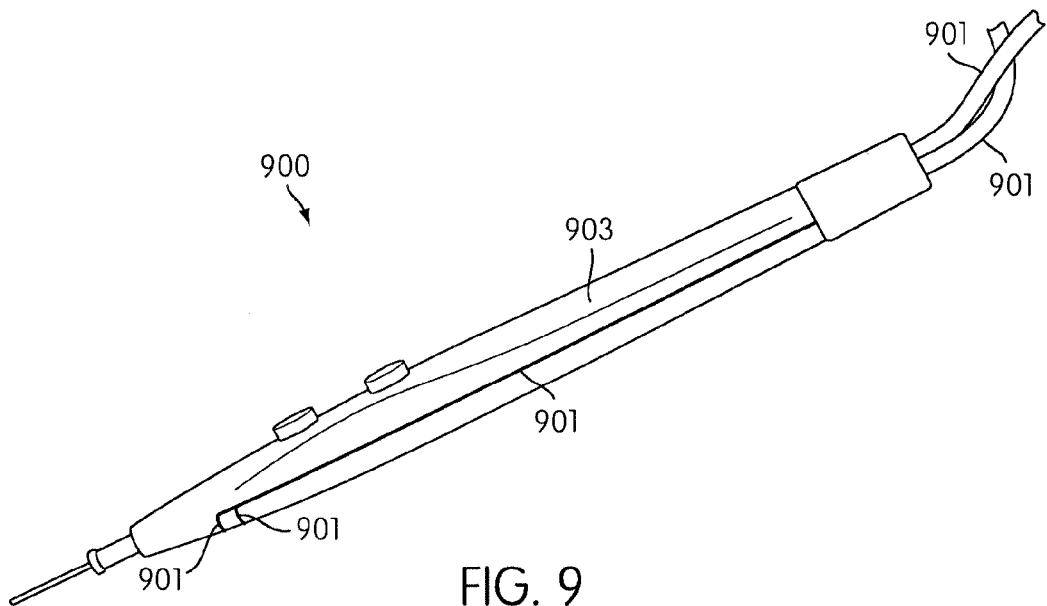
FIG. 9 illustrates an example of a tracked instrument according to various embodiments of the invention.

Another example of a tracked instrument 129 that may be used with integrated system 100 is a Bovey device or other electrocautery device onto which one or more position indicating elements have been attached or integrated. FIG. 7 illustrates a Bovey device 700, having an electrocautery tip 701 and that includes two perpendicularly oriented position indicating elements 703 embedded in the body 705 of the device located near the electrocautery tip 701, along with leadwires 707 that run along body 705 of the device. FIG. 8 illustrates the body 800 of a Bovey device with two position indicating elements 801 embedded therein, perpendicular from one another. FIG. 9 illustrates a Bovey device 900, wherein two leadwires 901 each from a position indicating element embedded therein are joined together as they run along the body 903 of the device.

Figure 10A:
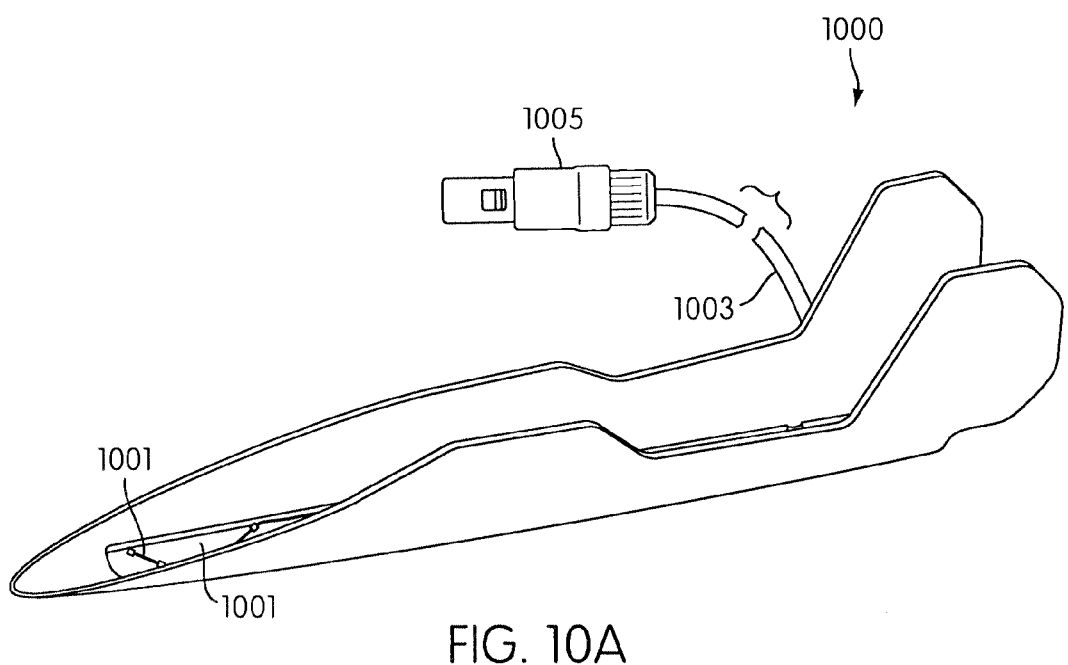
FIG. 10A illustrates an example of a tracked instrument according to various embodiments of the invention.
Figure 10B:
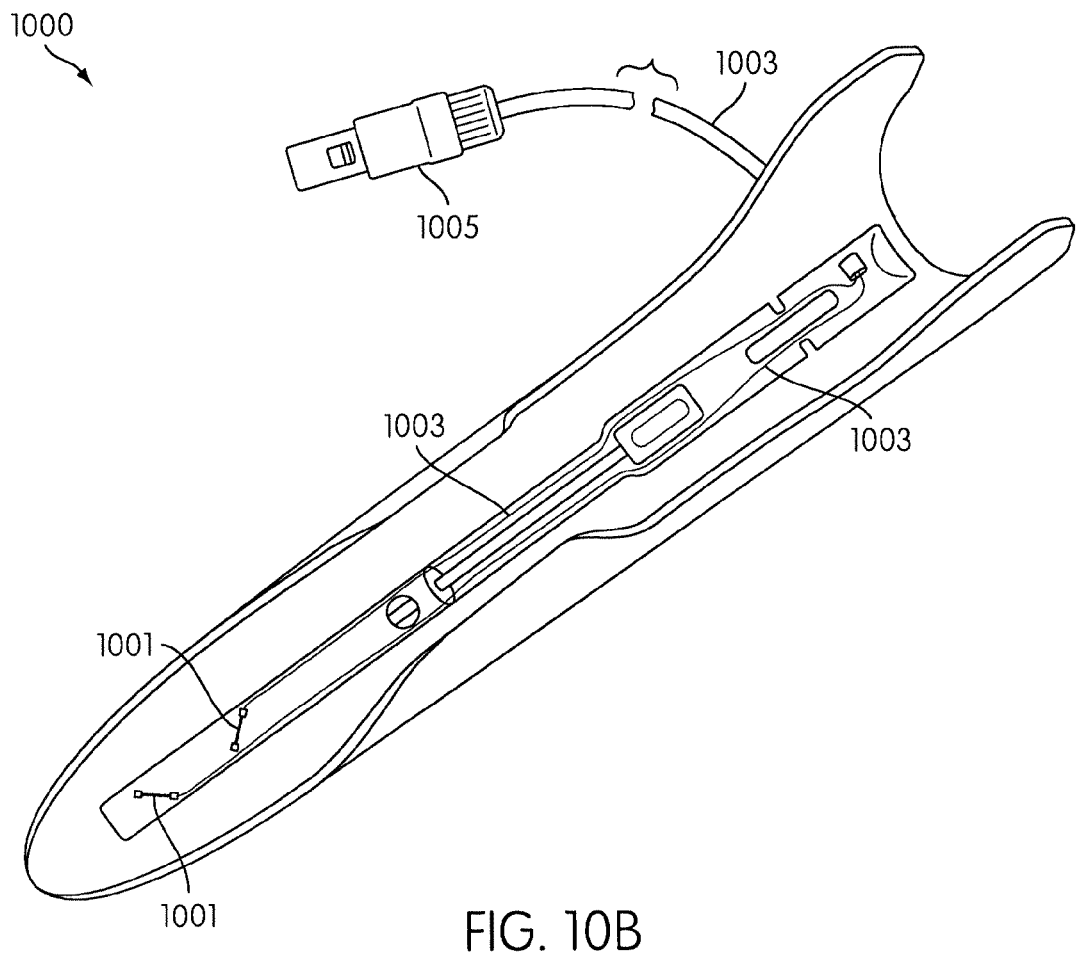
FIG. 10B illustrates an example of a tracked instrument according to various embodiments of the invention.

Another example of a tracked instrument 129 that may be used with integrated system 100 is an ultrasound needle guide (such as one manufactured by Civco Medical Instruments, Kalona, Iowa) onto which one or more position indicating elements have been attached. FIGS. 10A and 10B illustrate an endorectal needle guide 1000 that includes two perpendicularly oriented position indicating elements 1001 attached thereto. Needle guide 1000 may be removably attached to a matching ultrasound transducer allowing the transducer location and orientation to be tracked. Needle guide 1000 may also include leadwires 1003 that run along the body of the instrument, ultimately extend off of the body of the instrument, and terminate at an interface 1005. Position indicating elements 1001 enable integrated system 100 to determine the position and/or orientation of the tip of needle guide 1000 or to determine the position and/or orientation of other instruments such as, for example the scan plane of an ultrasound. This may enable determination of the relative spatial position of an instrument to the ultrasound scan plane to determine, for example, the intersection between the instrument's trajectory and a scan plane. Tracking an ultrasound transducer may enable coordinated or "fused" CT/ultrasound or MR/ultrasound visualization of a target, in which a preoperative CT or MR scan is reformatted along a plane determined by the ultrasound transducer's location and orientation. This would allow a CT or MR to be displayed in a format matching the ultrasound providing additional information from the preoperative scan to be superimposed on the live ultrasound. For example, a lesion visible only under MR could be projected onto the live ultrasound view.

Figure 11A:
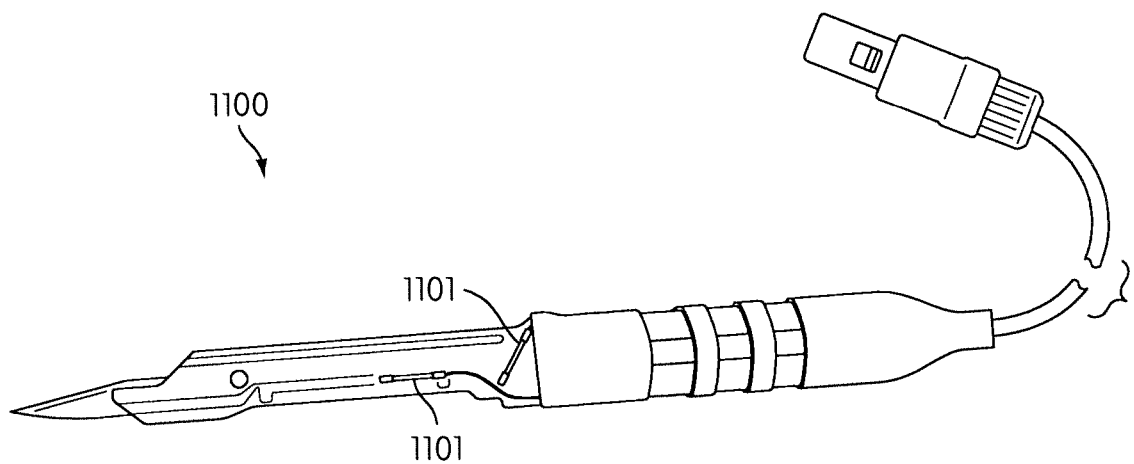
FIG. 11A illustrates an example of a tracked instrument according to various embodiments of the invention.
Figure 11B:
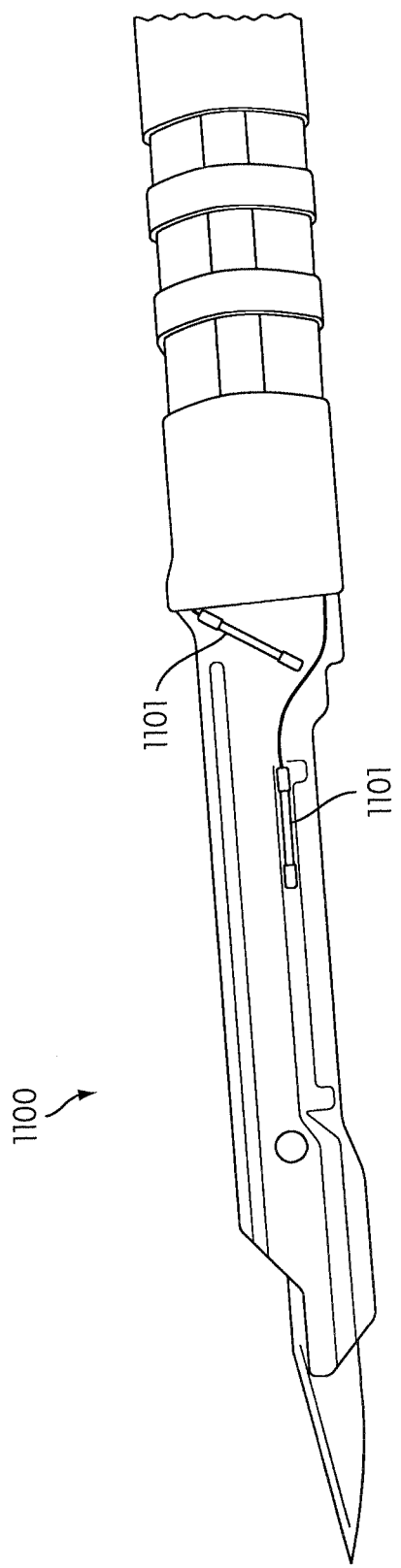
FIG. 11B illustrates an example of a tracked instrument according to various embodiments of the invention.

Another example of a tracked instrument 129 that may be used with integrated system 100 is a scalpel onto which one or more position indicating elements have been attached. FIGS. 11A and 11B illustrate a scalpel 1100 that includes two oriented position indicating elements 1101 integrated therein. The trackable position indicating elements 1101 enable the tip and cut plane of scalpel 1100 to be determined using integrates system 100. This may assist a physician in determining the location to begin an incision.

Figure 12A:
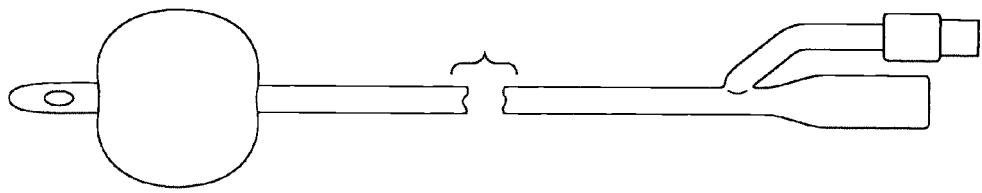
FIG. 12A illustrates an example of a Foley catheter.
Figure 12B:
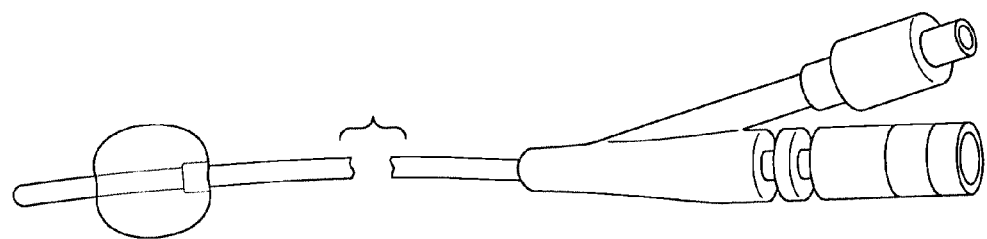
FIG. 12B illustrates an example of a Foley catheter.

FIGS. 12A and 12B illustrate instruments 1200a and 1200b, which are examples of Foley catheters. A Foley catheter is a device used in various situations to control urine drainage from the bladder, it is widely used, is highly effective, and has low complication rates. In some embodiments, Foley catheters may be used to assist in diagnosing, planning treatment of, and treating prostate cancer or other diseases or conditions.

Figure 12C:
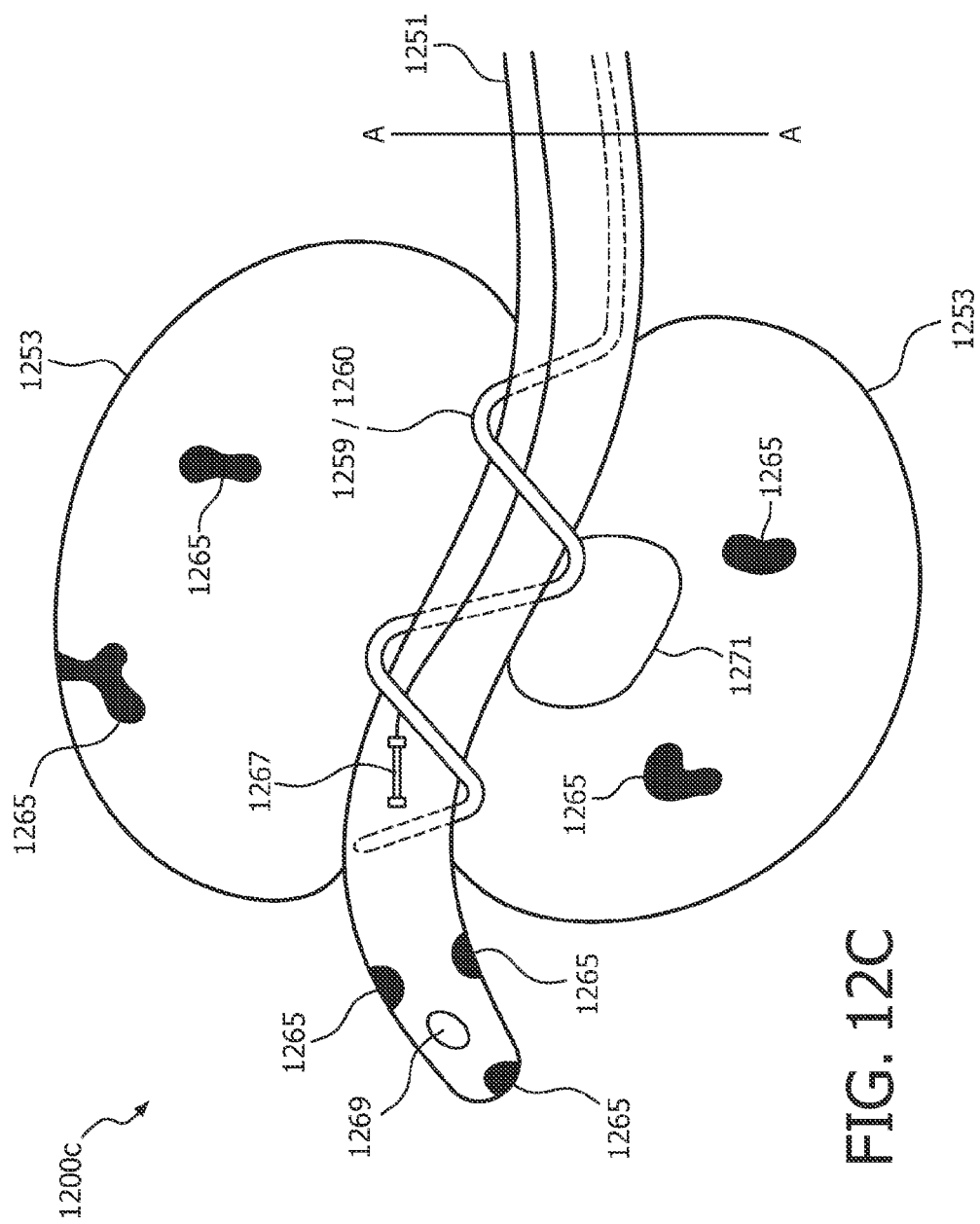
FIG. 12C illustrates an example of catheter device according to various embodiments of the invention.

An example of a portion of a Foley catheter is shown in FIG. 12C, which illustrates a distal portion of a catheter 1200c according to various embodiments of the invention. In some embodiments, catheter 1200c that may include a catheter portion 1251, a balloon portion 1253, and/or other portions or elements. The description herein includes a modified Foley catheter for use with the invention, but a catheter with some or all of the features described herein my be used instead of a Foley catheter.

Figure 12D:
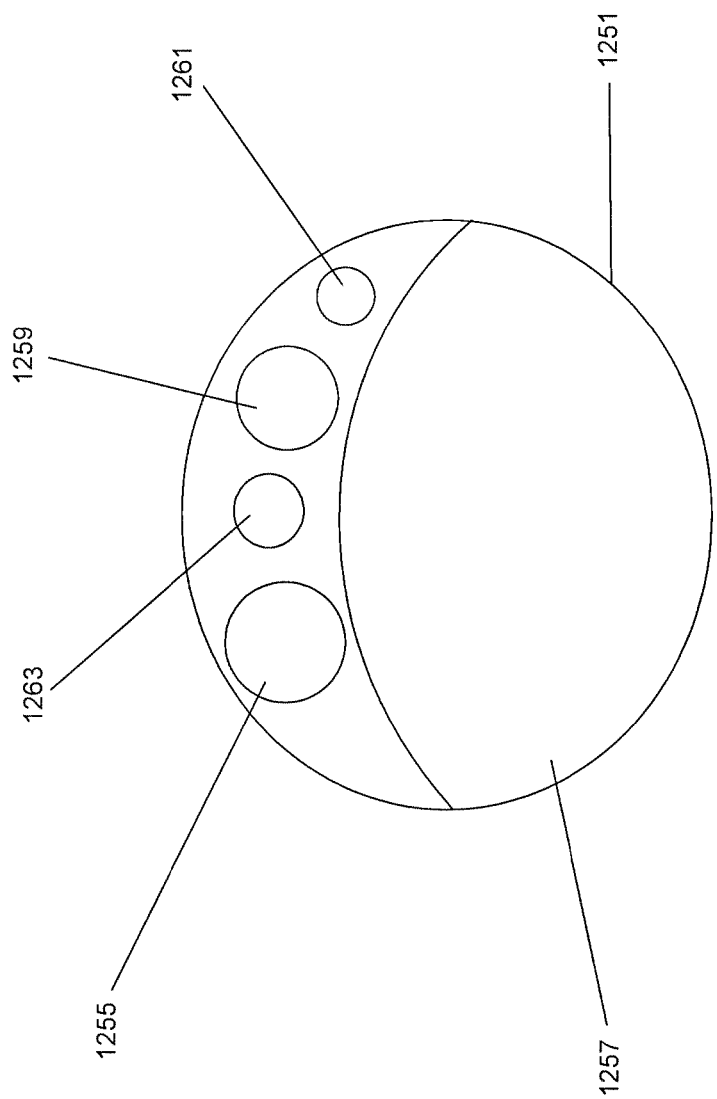
FIG. 12D illustrates an example of a cross section of a catheter device according to various embodiments of the invention.

FIG. 12D illustrates a cross section at line A-A of the tubular portion of catheter 1200c. As illustrated in FIG. 12D, in some embodiments, a catheter used with the invention includes an inflation lumen 1255 for inflating a balloon (e.g., balloon 1253), a drainage lumen 1257 for draining of urine or other fluid from a portion of a patient's anatomy (drainage lumen 1257 may include an opening 1269 at the distal end of catheter 1251 to enable urine or other fluid to enter drainage lumen 1257), a "Registration Path" lumen 1259 for insertion and use of a registration device (e.g., registration device 121) or for other uses (e.g., for introducing material visible to an imaging modality), an image coil lumen 1261 for inserting an MR (or other type of imaging modality) coil into the anatomy of a patient, tracked wire lumen 1263 for accommodating a wire equipped with one or more position indicating elements (which my be registration devices, dynamic referencing devices, or other devices), and/or other lumens. In some embodiments, catheter 1200c may have more or less lumens than described herein. In some embodiments, one or more of the lumens of catheter 1200c may be multipurpose and may perform several functions. For example, in some embodiments, a guidewire having one or more position indicating elements attached thereto or incorporated therein may be passed along one or more of the lumens described. In some embodiments a single lumen may be used for drainage, accommodation of registration devices, accommodation of dynamic referencing devices, and/or accommodation of other devices.

In some embodiments, catheter 1200c may include additional features. For example, in some embodiments, balloon 1253 and/or catheter portion 1251 may include one or more markings 1265, which may be visible to an imaging device (e.g., imaging device 127). In some embodiments, catheter portion 1251 may include multiple lumens in one or more of drainage lumen 1257, inflation lumen 1255, and/or other lumens. In some embodiments, catheter portion 1251 may include one or more position indicating elements 1267 that may be permanently embedded or removably embedded in the distal tip of the instrument (e.g., near balloon 1253 of catheter 1200c) and any leadwires associated therewith.

Figure 13:
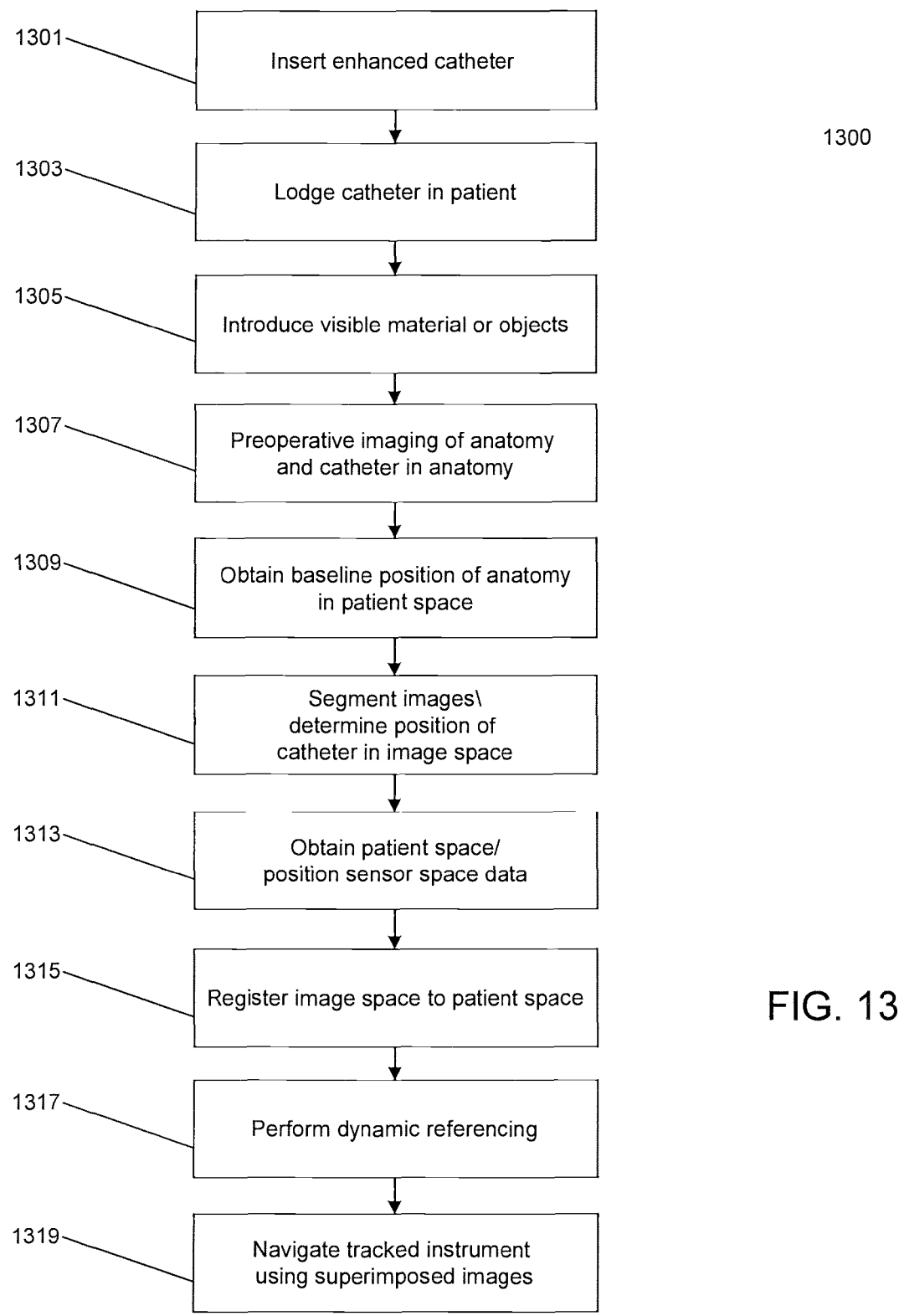
FIG. 13 illustrates an example of a process according to various embodiments of the invention.

FIG. 13 illustrates a process 1300, which is an example of a process for using an enhanced catheter to obtain image and/or patient space data necessary for an image guided procedure on the prostate or other anatomy of a patient, for performing a registration of image space and patient space data of the prostate or other anatomy of the patient, and/or for guiding tracked instruments to the prostate or anatomy of the patient.

In an operation 1301, an enhanced catheter 1200c is inserted into the anatomy of the patient (e.g., into the anatomy near the prostate). In some embodiments, this insertion may occur just prior to imaging, surgery, or other procedure. In an operation 1303, the balloon 1253 of catheter 1200c is inflated, lodging catheter portion 1251 into the anatomy of the patient (e.g., in the opening of the bladder during prostate surgery). This fixes the location of catheter 1200c so that it is relatively immobile near the fixation point.

In an operation 1305, a substance or object may be introduced into registration path lumen 1259 or other lumen of catheter 1200c, rendering at least parts of catheter 1200c visible under an imaging modality (e.g., imaging device 127). In some embodiments, a path of catheter 1200c may be made visible to the imaging modality through introduction of appropriately visible materials such as, for example gadolinium ("Gd") or other visible material. In some embodiments, one or more objects visible to the imaging modality may be introduced into catheter 1200c. The Gd or other visible material or objects may be placed into a lumen of catheter 1200c such as, for example, registration path lumen 1259 or other lumen.

In some embodiments, the visible material or objects may be introduced after a preoperative diagnostic scan (described below) so as not to obscure images of the prostate or other area of interest. In some embodiments, the visible material or objects may be introduced prior to or during the preoperative diagnostic scan. In some embodiments, material or objects visible to the imaging modality need not be introduced into catheter 1200c, if for example, catheter 1200c includes a lumen in which Gd or other visible material or objects are already present or if catheter 1200c itself can be visualized inside the anatomy of the patient by the imaging modality without the such of such material.

In some embodiments, additional visible elements such as fiducial markings 1265 (which may include discrete or continuous fiducial patterns) that are visible to the imaging modality may be incorporated in or onto one or more of balloon 1253, the body of catheter portion 1251, or other portion of catheter 1200c. These additional visible elements may render at least part of the fixed distal portion of catheter 1200c visible under the imaging modality.

In some embodiments, the additional visible elements may include one or more fiducial markings that are radio-opaque length markings that are visible to computerized tomography imaging modalities, magnetic resonance imaging modalities, or other imaging modalities.

In some embodiments, the additional visible elements may be present in a removable stylet. The removable stylet may be placed on catheter 1200c prior to inserting catheter 1200c into the anatomy of the patient. In some embodiments a medical professional or other operator may have access to a plurality of removable stylets with visible elements incorporated therein. The different stylets within the plurality of stylets may have visible elements made of materials that are visible to different imaging modalities or different sets of imaging modalities. That way, if a certain procedure dictates that a specific type of imaging modality (or modalities) is used, the medical professional or other operator may select and attach the stylet having visible elements thereon made from materials best suited for the specific imaging modality (or modalities). In some embodiments, the removable stylets may include a micro magnetic resonance imaging coil for obtaining additional image space data regarding the anatomy of the patient 9 or for use as a position indicating element).

In some embodiments, these additional visible elements may form a pattern in or on part of balloon 1253. For example, in some embodiments, the additional elements may include one or more sub-balloons 1271 inside main balloon 1253. In some embodiments, the one or more sub-balloons 1271 may contain or be inflated with a substance that is visible under the imaging modality. In some embodiments, the one or more sub-balloons may be inflated using a lumen separate from inflation lumen 1255 (so as to enable the introduction of a fluid separate from the fluid used to inflate balloon 1253).

In some embodiments, the additional visible elements may include a special path/lumen 1260 that may be housed within balloon 1253, interior to catheter 1200c, or that otherwise forms part of catheter 1200c. The special path/lumen 1260 may form a pattern such as, for example, a spiral or other tortuous pattern that can be made visible through the introduction of a contrast agent. In some embodiments, the special path lumen 1260 may be part of registration path lumen 1259 (FIG. 12D). In some embodiments, catheter 1200c may be manufactured such that registration path lumen 1259 may be deliberately tortuous in one or more areas of catheter portion 1251. FIG. 12C illustrates registration path lumen 1259 that takes a tortuous (e.g., spiral) path within balloon 1253. In some embodiments, other parts of regisration path lumen 1259 may be tortuous. In some embodiments, the tortuous path taken by registration lumen 1259 may be different that that illustrated in FIG. 12C.

Other visible elements may be used that render part of balloon 1255 and/or catheter portion 1251 visible to the imaging modality. In some embodiments, additional non-integrated elements that are not associated with catheter 1200c may be applied to the anatomy of the patient such as, for example, needles or skin markers that are visible to the imaging modality that are placed on or onto the patient nearby to the prostate or other point of interest.

In an operation 1307, preoperative diagnostic images (or other preoperative images) of the anatomy of the patient and the catheter (e.g., the portions of the catheter visible to the imaging modality). In some embodiments, a preoperative diagnostic scan MR scan or other preoperative diagnostic scan may be performed using a micro imaging coil placed within catheter 1200c (e.g., within an image coil lumen 1261 or other lumen of catheter 1200c), which enables enabling imaging of the surrounding tissue and the visible elements of the catheter. In some embodiments, preoperative diagnostic images may be obtained using an MR scan or other scan that is performed using traditional, exteriorly placed surface imaging coils, endorectal coils, or a combination of multiple coils (e.g., some internal to the patient, some external to the patient). Both the internal preoperative diagnostic images and the external preoperative diagnostic images may be considered "image space data" (or may be used to obtain image space data). This image space data may be stored in integrated system 100 for use in image-guided surgery. In some embodiments, multiple preoperative imaging modalities may be used.

In some embodiments, the micro imaging coil within catheter 1200c may also serve a second purpose as a position indicating element (as described herein) for obtaining patient space data using a tracking system.

If more than one preoperative image has been obtained (e.g., an internal MR scan using an imaging coil within catheter 1200c, and an MR scan using an MR device external to the patient), the multiple images may be co-registered. This may be done using mutual information, paired point, surface matching, path matching of the catheter itself or of some other body lumen or other methods known in the art. The co-registered images may comprise the images space data used in the invention.

In some embodiments, before or during prostate procedures or other procedures, the catheter 1200c when used with an image-guided surgery system such as, for example, integrated system 100, may aid or enable performance of registration and/or dynamic referencing of the anatomy of the patient for the purposes of using image guidance to perform the procedure. As such, catheter 1200c may be utilized, alone or in conjunction with other devices, to obtain location and/or orientation information in position sensor space (patient space) of one or more position indicating elements, wherein the position sensing elements are in a known spatial relationship with elements of catheter 1200c that are visible to the imaging modalities used to obtain the image space data (e.g., gadolinium, fiducial elements or other visible objects or material), such that the image space data may be registered to the position sensor space data, thus, enabling tracked tools to be navigated using the preoperative images. However, in some embodiments, catheter 1200c may be removed after the image space data is obtained, and a second catheter may be introduced into the anatomy of the patient. In some embodiments, the second catheter may be a Foley catheter or other type of catheter. The second catheter may one or more include position indicating elements which, once in place, may be in a known spatial relationship with the elements of catheter 1200*c* that are visible to the imaging modalities used to obtain the image space data. The position and/or orientation of the position sensing elements of the second catheter may then be obtained to generate position sensor space data, which may then be registered to the image space data, thus, enabling tracked tools to be navigated in the anatomy of the patient using the preoperative images.

In an operation 1309, the position of the catheter in the anatomy of the patient may be sampled in patient space (also referred to herein as "position sensor space") to obtain a baseline position of the anatomy. In some embodiments, the catheter's position in patient space may be sampled prior to making any significant changes to the patients position relative to the preoperative diagnostic images. In some embodiments, an endorectal coil (e.g., and MR coil for obtaining image space data form a perspective internal to the anatomy of the patient) may have been introduced into the anatomy of the patient, and the catheter's position in patient space may be sampled prior to removing the endorectal coil.

In an operation 1311, the image data of the pathway of the fixed distal portion of catheter 1200*c* or other image data of portions of or objects on catheter 1200*c* that are visible to the imaging modality (e.g., fiducial markings 1265, sub-balloon 1271, a visible tortuous path, or other visible elements) may then be segmented using intensity or other segmentation methods known in the art and the position of catheter 1200*c* (or parts thereof) may be determined in image space. Segmentation renders the coordinates of paths, fiducial elements, or other visible elements known in the image space coordinate system, which is a prerequisite to performing registration. The segmentation may additionally be used to determine the location of path centroids or centroids of fiducial elements or other visible elements in image space to obtain better estimates for the actual location of the images objects. Frequently, images of fiducial elements appear indistinct or blurry. A better estimate of the center of the object can be determined by calculating its centroid.

Once the positions of the imageable portions of catheter 1200*c* are obtained in image space, their spatial position and/or orientation in patient space (i.e. position sensor space) may be obtained in an operation 1313. In some embodiments, the position sensor space information may be done by using a drag-back method as described in U.S. Patent Publication No. 20050182319, entitled "Method and Apparatus for Registration, Verification, and Referencing of Internal Organs (U.S. patent application Ser. No. 11/059,336), which is hereby incorporated by reference herein in its entirety, by placing a tracked guidewire or similar device (e.g., registration device 121 or other device having one or more position indicating elements therein) into catheter 1200*c* (e.g., into "Registration Path" lumen 1259) and sliding it over the registration zone, i.e. the zone close to where catheter 1200*c* is imageable, usually at the distal end close to the lodged balloon 1255. As the guidewire is slid, a locus of position sensor space points are obtained that are representative of the path that can be matched with the image space path to perform registration.

In some embodiments, the position sensor space information may be obtained using the drag-back method in conjunction with the elements within balloon 1255 (e.g. the registration device may be dragged back or otherwise moved within a spiral or tortuous pathway or pathway of another pattern that exists within balloon 1255). These elements may be similar to or the same elements that are imageable and used to obtain the image space information regarding catheter 1200*c*.

In some embodiments, the position sensor space information may be obtained using a method such as 2D-3D where the 2D technique is from two or more x-rays and the 3D is an MR scan. This method is disclosed by Dotan Knaan, Leo Joskowicz: *Effective Intensity-Based 2D/3D Rigid Registration between Fluoroscopic X-Ray and CT*. MICCAI (1) 2003: 351-358, which is hereby incorporated by reference herein in its entirety.

In some embodiments, position sensor space information may be obtained by using a tracked calibrated ultrasound transducer such as, for example, a tracked endorectal transducer (having one or more position indicating elements thereupon), to identify landmarks in the patient and in the preoperative images. Because the ultrasound is calibrated and tracked by a tracking device (e.g., tracking device 127), the location of the selected points in the ultrasound scan plane is known in the position sensor space. In some embodiments, the landmarks used to obtain position sensor space information may be in or part of catheter 1200*c* and may be different or the same as the elements visible to the imaging modalities used to obtain preoperative image space information (e.g. the fiducial elements or other visible elements). Methods of ultrasound calibration are known in the art. Many methods of calibration exist, some of which are summarized in the document "3*D Ultrasound Probe Calibration Without A Position Sensor*" by A. H. Gee, N. E. Houghton, G. M. Treece, and R. W. Prager; CUED/FINFENG/TR 488 September 2004 (Cambridge University, Department Of Engineering, Trumpington Street, Cambridge CB2 1PZ, United Kingdom) and in the document "*Probe Calibration for Freehand* 3-*D Ultrasound*" by F. Lindseth, G. A. Tangen, T. Lango, and J. Bang; both of which are hereby incorporated by reference herein in their entirety.

In some embodiments, the position sensor space information may be obtained by physically touching registration points (e.g., those close to or at the imageable portions of catheter 1200*c*) on or in the patient with a tracked device and measuring/sampling the position of the device when the points are touched (e.g., point registration).

In some embodiments, the registration is effected by manually positioning the ultrasound image so as to coincide with the other imaging modalities used. This may be accomplished by manually "dragging" the images from one modality on a display screen (e.g., display 117) so that they optimally overlay the images of the other modality.

In some embodiments, the position sensor space information may be obtained by introducing a device containing position indicating elements in a known spatial relationship to the fiducial elements or other elements visible to the imaging modality that were visible in catheter 1200*c* at the time of the preoperative imaging. For example, a position sensing tube containing position sensing elements that exactly overlap fiducial elements (visible to an imaging modality) in catheter 1200*c* may be introduced into the anatomy of the patient, thereby giving patient space location of the fiducial elements visualized in image space. Other spatial relationships of position indicating elements to the fiducial elements are also possible.

In an operation 1315, the image space information and the patient space information (position sensor space information) may be registered to one another to register the portion of the anatomy of the patient near to the point of interest (e.g., the prostate) for the purposes of image guided surgery.

In an operation, 1317, dynamic referencing may be performed by fixating position sensing elements in balloon 1255 or a lumen of catheter 1200*c* (e.g., dynamic referencing lumen 1263) that is attached to the lodged part of catheter 1200c. In some embodiments, fixation of position sensing elements used for dynamic referencing may be performed concurrent with or prior to operation 1313. Dynamic referencing tracks the motion of the organ or other anatomy of the patient during a treatment. In some embodiments, the position sensing elements used for registration may be used for dynamic referencing. In some embodiments, the lumen used for dynamic referencing may be the same as that used for registration.

In an operation 1319, a therapeutic instrument 129 or other tracked tool may be inserted into the anatomy of the patient (e.g., the prostate, during prostate surgery) and navigated using a graphical overlay of the tracked portion of the instrument superimposed on the preoperative images (e.g., the images obtained in operation 1307) which may be enabled by one or more modules 111a-111n of integrated system 100 and displayed on display device 117. Therapeutic instrument 129 or other tracked instrument may include, for example, one or more of a tracked radiofreqency ablation button as described by Glossop and Wood in U.S. Provisional Patent Application No. 60/625,186 and International Publication No. WO 2006/057786 which is hereby incorporated by reference herein in its entirety, a tracked cryo-therapy probe, a tracked microwave device, a tracked high definition radiation therapy (HDRT) needle, a tracked needle or insertion of brachytherapy seeds (and other uses), a tracked scalpel (e.g., scalpel 1100), a tracked harmonic scalpel (e.g., harmonic scalpel 200 or 300), a tracked clamp (e.g., clamp 500 or 600), a tracked Bovey device or other electrocautery device (e.g., Bovey device 700 or 900), a tracked endorectal needle guide (e.g., needle guide 1000), and/or other tracked instrument.

In some embodiments, after catheter 1200c is inserted in to the anatomy of the patient (e.g., operation 1301), the patient's anatomy and the visible portions of catheter 1200c therein may be imaged using two different imaging modalities, wherein the visible portions of the catheter are visible to both imaging modalities or separately rendered visible to both imaging modalities. The images from both of the two imaging modalities are used to provide image space data regarding the visible portions of catheter 1200c (e.g., the two sets of image space data may be co-registered). In some embodiments, the first of the two imaging modalities may be a magnetic resonance imaging modality and the second of the two imaging modalities may comprise a tracked ultrasound device that includes one or more position indicating elements thereon, wherein the position indicating elements can be tracked by a tracking device (e.g., tracking device 125). The coordinates of the visible portion of catheter 1200c may then be determined using the tracking device to obtain patient space data. The patient space data may then be registered to the image space data for use in guiding a tracked instrument (an instrument equipped with one or more position indicating elements tracked by the tracking device) during an image guided procedure. In some embodiments, the image guided procedure utilizes a dynamic graphic overlay of reformatted magnetic resonance images on ultrasound images. In some embodiments, the magnetic resonance images are reformatted in the same plane as the ultrasound images. In some embodiments, the ultrasound images are obtained using an endorectal ultrasound transducer.

Figure 14A:
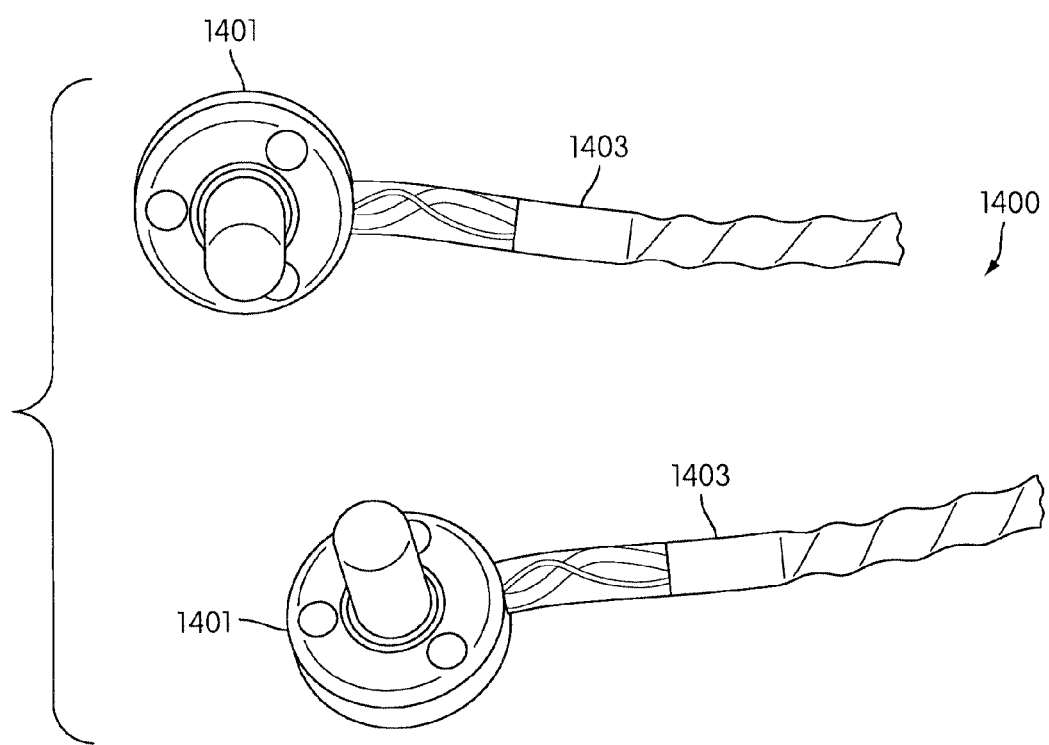
FIG. 14A illustrates an example of a skin patch device according to various embodiments of the invention.
Figure 15:
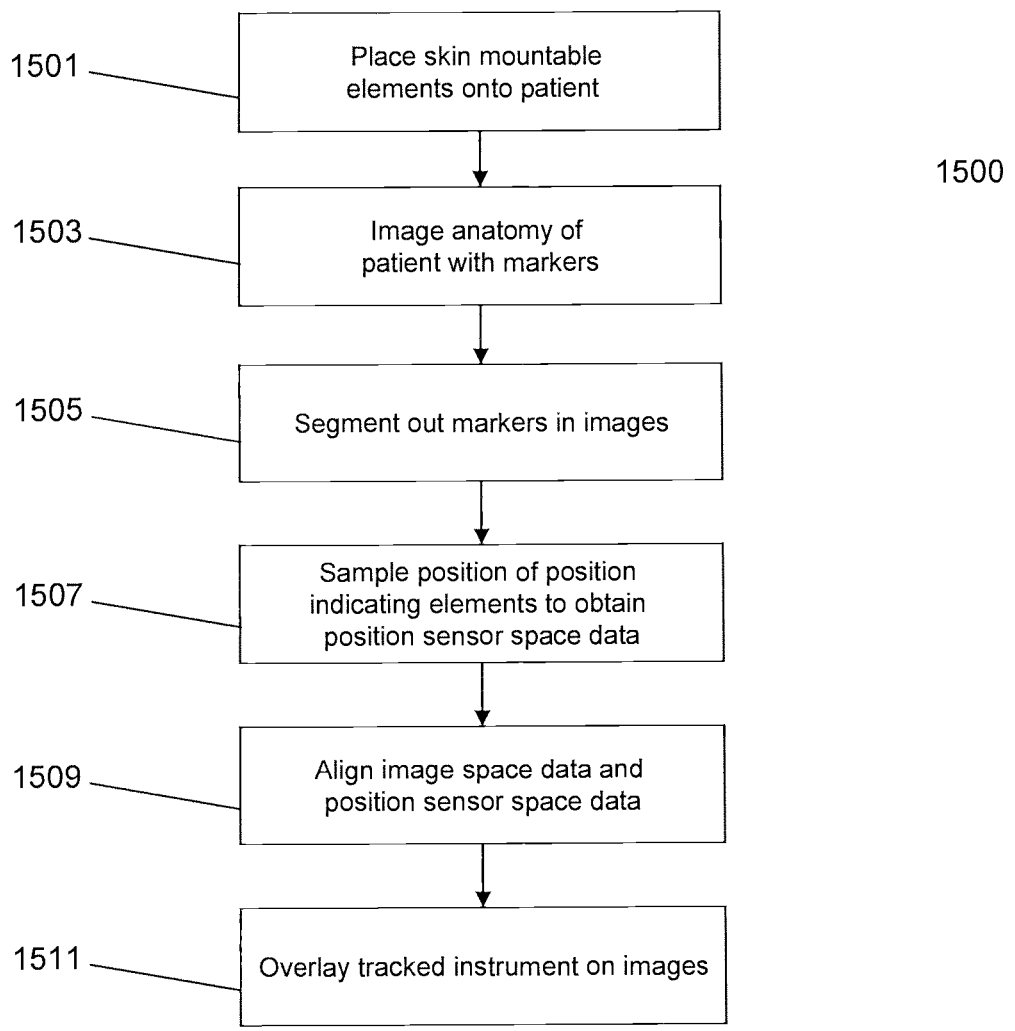
FIG. 15 illustrates an example of a process according to various embodiments of the invention.

FIGS. 14A and 14B illustrate a skin patch device 1400, which is a device that may be used for purposes of registration, dynamic referencing, and/or for other purposes in image guided surgery with integrated system 100. In some embodiments, skin patch device 1400 comprises a plurality of skin mountable elements and one or more position indicating elements embedded in a housing 1401. Housing 1401 can be placed on or into the skin or tissue of the anatomy of a patient. Housing 1401 include one or more markers that are visible to an imaging modality (e.g., imaging device 127). In some embodiments, skin patch device 1400 may also include lead wires 1403, an interface 1405 (e.g., for interfacing with integrates system 100 via an input 113), and/or other elements.

An example of a skin patch that may be used as part of the present invention is the skin patch described in U.S. Patent Publication No. 20060173269 (U.S. patent application Ser. No. 11/271,899), entitled "Integrated Skin-Mounted Multi-function Device for use in Image-Guided Surgery," which is hereby incorporated herein by reference in its entirety. As demonstrated by U.S. Patent Publication No. 20060173269, additional features may be present on the skin patch.

FIG. 1500 includes a process 1500 wherein a skin patch device (e.g., skin patch device 1400) may be used for image guided surgery. In some embodiments, process 1500 may include an operation 1501, wherein the plurality of skin mountable elements (e.g., housing 1401 and its contents) of a skin patch device are placed onto the skin of a patient. In one embodiment, the skin mountable elements, and thus the position indicating elements and the markers that are visible to an imaging modality contained in the housing, are placed in a pattern around a site of interest of the anatomy of the patient, which in some embodiments, may be inside the anatomy of the patient. In some embodiments, markers visible to an imaging modality and position indicating elements may be placed around the site of interest using one or more skin mountable elements and one or more devices insertable into the anatomy of the patient (e.g., needles, catheters, or wires) that include one or more markers visible to an imaging modality and one or more position indicating elements. Such skin patches may be used to perform registration either alone or to assist in mathematically constraining the calculations in the catheter based registration described above, by providing an initial estimate of the position and orientation of the anatomy that can be used as an initial estimate in the calculation of a registration matrix.

In an operation 1503, images of the anatomy of the patient including the site of interest are then taken with the markers and position indicating elements in place. In an operation 1505, the markers' location and geometry are then segmented from the images, so as to determine the position and orientation of each of the position sensing elements in image space.

In an operation 1507, the positions and orientations of the position indicating elements are then measured/sampled using a tracking device (e.g., tracking device 125) to obtain position sensor space data of these elements. In an operation 1509, the measured image data and the measured/sampled tracking device data are used to create a registration matrix using one or more methods such as, for example, singular value decomposition (SVD), iterative closest points (ICP), the methods taught by Fitzpatrick in U.S. Patent Publication No. 20060147100 (U.S. patent application Ser. No. 10/543, 706) entitled "Apparatus and Methods of Determining Marker Orientation in Fiducial Registration," which is hereby incorporated by reference herein in its entirety, or other methods.

The images of operation 1503 may be loaded onto an integrated system or image guided surgery workstation similar to that described in U.S. Patent Publication No. 20050182319, which was previously incorporated by reference. The registration matrix produced in operation 1511 may be used, in an operation 1513, to guide a tracked instrument (e.g., therapeutic instrument 129) in the anatomy of a patient for image guided surgery or other image guided procedures by overlaying an indication of the position of the tracked instrument onto images of the anatomy (e.g., the images of operation 1503).

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A method for aiding the performance of an image guided procedure, comprising:
    inserting a catheter device into an anatomy of a patient, the catheter device including a catheter portion having a plurality of lumens therein, and a balloon portion;
    inflating the balloon portion by passing a fluid through at least one of the plurality of lumens that is in fluid communication with the balloon portion, so that the catheter device is removable fixed within the anatomy of the patient;
    imaging the anatomy of the patient using an imaging modality to obtain image space data of at least a portion of the catheter device visible to the imaging modality,
        wherein the at least a portion of the catheter device visible to the imaging modality includes a special path of the plurality of lumens exterior to the catheter portion and housed within the balloon portion, and
        wherein the image space data includes a position of the at least a portion of the catheter device within the anatomy of the patient;
    inserting a registration device having at least one position indicating element into a registration path lumen of the plurality of lumens to obtain patient space data of the anatomy of the patient using a tracking device;
    inserting a dynamic referencing device into a dynamic referencing lumen of the plurality of lumens of the catheter device to dynamically reference the anatomy of the patient during the image guided procedure, the dynamic referencing lumen being distinct from the registration path lumen; and
    registering the image space data to the patient space data for use during an image guided procedure to the anatomy of the patient.

2. The method of claim 1, wherein the special path of the plurality of lumens is treated with a material visible to the imaging modality.

3. The method of claim 2, wherein the special path of the plurality of lumens is treated with the material visible to the imaging modality prior to insertion of the catheter device into the anatomy of the patient.

4. The method of claim 2, wherein the special path of the plurality of lumens is treated with the material visible to the imaging modality after insertion of the catheter device into the anatomy of the patient.

5. The method of claim 1, wherein the special path of the plurality of the lumens forms a pattern visible to the imaging modality when a material visible to the imaging modality is introduced into the special path.

6. The method of claim 5, wherein the pattern includes a tortuous pattern.

7. The method of claim 1, wherein the portion of the catheter device visible to the imaging modality further includes one or more fiducial markings of a material visible to the imaging modality.

8. The method of claim 7, wherein the one or more fiducial markings include one or more radio-opaque length markings that are visible to one or more of computerized tomography imaging modalities and magnetic resonance imaging modalities.

9. The method of claim 7, wherein the one or more fiducial markings are present on a removable stylet that is selectively placed on the catheter device prior to inserting the catheter device into the anatomy of the patient, and wherein the removable stylet is chosen from a plurality of removable stylets according to the type of imaging modality used to image the anatomy of the patient.

10. The method of claim 9, wherein the removable stylet includes a micro magnetic resonance imaging coil to obtaining additional image space data regarding the anatomy of the patient.

11. The method of claim 7, wherein the fiducial markings are present on the balloon portion of the catheter device.

12. The method of claim 1, wherein the registration device includes one or more position indicating elements in a known spatial relationship to the at least a portion of the catheter device visible to the imaging modality.

13. The method of claim 1, further comprising inserting a micro-imaging coil into at least one of the plurality of lumens to obtain additional image space information regarding the anatomy of the patient.

14. The method of claim 13, wherein registering the image space data to the patient data comprises co-registering the additional image space data to the image space data prior to registering the image space data to the patient space data.

15. The method of claim 1, wherein the registration path lumen includes the special path.

16. A method for aiding the performance of an image-guided procedure, comprising:
    inserting a catheter device into an anatomy of a patient, the catheter device including a catheter portion having a plurality of lumens therein and a balloon portion;
    inflating the balloon portion by passing a fluid through at least one of the plurality of lumens that is in fluid communication with the balloon portion so that the catheter device is removable fixed within the anatomy of the patient;
    rendering at least a portion of the catheter device visible to a first imaging modality;
    imaging the anatomy of the patient using an imaging device to obtain image space data of a first portion of the catheter device rendered visible to the first imaging modality,
        wherein the first portion of the catheter device visible to the imaging modality includes a special path of the plurality of lumens exterior to the catheter portion and housed within the balloon portion, and
        wherein the image space data includes the position of the first portion of the catheter device within the anatomy of the patient;
    rendering the first portion of the catheter device visible to a second imaging modality;
    imaging the first portion of the catheter device with the second imaging modality, wherein the second imaging modality includes one or more position indicating elements whose position is tracked by a tracking device;
    inserting a dynamic referencing device into a dynamic referencing lumen of the plurality of lumens of the catheter device to dynamically reference the anatomy of the patient during the image guided procedure;
    determining coordinates of the first position of the catheter device in a coordinate system of the tracking device, the coordinates comprising patient space data; and registering the imaging space data to the patient space data for use during an image guided procedure to the anatomy of the patient.

17. The method of claim 16, wherein the first imaging modality is a magnetic resonance imaging modality and wherein the second imaging modality is an ultrasound imaging modality.

18. The method of claim 17, wherein the image guided procedure utilizes a dynamic graphic overlay of reformatted magnetic resonance images on ultrasound images.

19. The method of claim 18, wherein the magnetic resonance images are reformatted in the same plane as the ultrasound images.

20. The method of claim 18, wherein the ultrasound images are obtained using an endorectal ultrasound transducer.

21. The method of claim 16, wherein a registration path lumen of the plurality of lumens includes the special path.

22. An image guided system, comprising:
   a image guided system for aiding the performance of an image guided procedure, the image guided system including
      a catheter portion having first and second ends and a plurality of lumens,
      a balloon portion at the second end of the catheter portion that, when inflated, removably fixes the image guided system into a portion of an anatomy of a patient,
         wherein at least a portion of the catheter device includes a special path of the plurality of lumens exterior to the catheter portion and housed within the balloon portion;
   a registration device accommodated within a first lumen of the plurality of lumens, the registration device having a first set of one or more position indicating elements for providing patient space data regarding the second end of the catheter position using a tracking device;
   a referencing device accommodated within a second lumen of the plurality of lumens, the referencing device having a second set of one or more position indicating elements for dynamically referencing the portion of the anatomy of the patient, the second lumen being distinct from the first lumen; and
   a computer element operable to register image space data and the patient data for use during the performance of the image guided procedure, the image space data regarding an imaging of the portion of the anatomy of the patient and a portion of at least one of the plurality of lumens.

23. The image guided system of claim 22, further comprising:
   at least one image modality for imaging the portion of the anatomy of the patient and the special path of the plurality of lumens.

24. The image guided system of claim 23, wherein the special path of the plurality of lumens is rendered visible to a first imaging modality positioned outside the anatomy of the patient by removable insertion of a material visible to the imaging modality.

25. The image guided system of claim 23, wherein the imaging modality positioned outside the anatomy of the patient is a magnetic resonance imaging modality.

26. The image guided system of claim 23, wherein a first imaging modality positioned outside the anatomy of the patient is a magnetic resonance imaging modality and a second imaging modality is one of an ultrasound imaging modality, a computerized tomography (CT) imaging modality, a single photon emission computerized tomography (SPECT) imaging modality, and a positron emission tomography (PET) imaging modality.

27. The image guided system of claim 23, wherein the special path of the plurality of lumens is treated with a material that is visible to a first imaging modality positioned outside the anatomy of the patient.

28. The image guided system of claim 27, wherein the material that is visible to the first imaging modality is gadolinium.

29. The image guided system of claim 27, wherein the special path of the plurality of lumens is treated with the material that is visible to the first imaging modality prior to an insertion of the catheter device into the anatomy of the patient.

30. The image guided system of claim 27, wherein the special path of the plurality of lumens is treated with the material that is visible to the first imaging modality after insertion of the catheter device into the anatomy of the patient.

31. The image guided system of claim 30, wherein the special path of the plurality of lumens forms a pattern visible to a first imaging modality positioned outside the anatomy of the patient when the material is introduced into the lumen.

32. The image guided system of claim 31, wherein the pattern includes a tortuous pattern.

33. The image guided system of claim 31, wherein the special path of the plurality of lumens includes one or more fiducial markings of a material visible to a first imaging modality positioned outside the anatomy of the patient.

34. The image guided system of claim 22, wherein at least one of the plurality of lumens is visible under a second imaging modality.

35. The image guided system of claim 22, further comprising:
   an image coil accommodated within a third lumen for obtaining additional image data regarding the portion of the anatomy of the patient from within the anatomy of the patient.

36. The image guided system of claim 35, wherein the additional image space data is co-registered to the image space data prior to the image space data being registered to the patient space data.

37. The image guided system of claim 22, wherein special path of the plurality of lumens takes a tortuous path through the balloon portion.

38. image guided system of claim 22, wherein the first lumen includes the special path.

* * * * *